(12) United States Patent
Chen et al.

(10) Patent No.: US 9,376,395 B2
(45) Date of Patent: Jun. 28, 2016

(54) PHARMACEUTICAL COMPOSITIONS

(75) Inventors: Yu Chen, San Jose, CA (US); Lan Yang, Hangzhou (CN); Feiyu Feng, Hangzhou (CN); Qiufu Ge, Hangzhou (CN); Dianwu Guo, Hangzhou (CN); Yi Chen, Lexington, MA (US)

(73) Assignee: Purdue Pharmaceuticals Products L.P., Stamford, CT (US)

( * ) Notice: Subject to any disclaimer, the term of this patent is extended or adjusted under 35 U.S.C. 154(b) by 176 days.

(21) Appl. No.: 14/345,562

(22) PCT Filed: Sep. 14, 2012

(86) PCT No.: PCT/US2012/055277
§ 371 (c)(1),
(2), (4) Date: Nov. 3, 2014

(87) PCT Pub. No.: WO2013/040286
PCT Pub. Date: Mar. 21, 2013

(65) Prior Publication Data
US 2015/0183747 A1    Jul. 2, 2015

Related U.S. Application Data

(60) Provisional application No. 61/536,038, filed on Sep. 18, 2011, provisional application No. 61/602,408, filed on Feb. 23, 2012.

(51) Int. Cl.
| | | |
|---|---|---|
| *C07D 235/16* | (2006.01) |
| *A61K 47/40* | (2006.01) |
| *A61K 31/16* | (2006.01) |
| *A61K 31/4184* | (2006.01) |
| *A61K 9/00* | (2006.01) |
| *A61K 9/19* | (2006.01) |
| *A61K 47/48* | (2006.01) |

(52) U.S. Cl.
CPC ............ *C07D 235/16* (2013.01); *A61K 9/0019* (2013.01); *A61K 9/19* (2013.01); *A61K 31/16* (2013.01); *A61K 31/4184* (2013.01); *A61K 47/40* (2013.01); *A61K 47/48969* (2013.01)

(58) Field of Classification Search
CPC ........... A61K 2300/00; A61K 31/4184; A61K 31/366; A61K 31/4745; A61K 31/675; A61K 9/0019; A61K 31/165; A61K 31/167; A61K 31/19; A61K 31/196; A61K 31/282; A61K 31/395; A61K 31/513; A61K 31/65; A61K 31/661; A61K 31/7064; A61K 9/0014; A61K 31/16; A61K 31/192; A61K 31/343; A61K 31/404; A61K 45/06; A61K 31/136; A61K 31/445; A61K 31/495; A61K 31/4965; A61K 31/505; A61K 31/5375; A61K 31/551; A61K 31/365; A61K 31/4025; A61K 31/4427; A61K 31/4523; A61K 31/454; A61K 31/496; A61K 31/497; A61K 31/506; C07D 235/30; C07D 235/26; C07D 235/28; C07D 239/10; C07D 239/46; C07D 239/47; C07D 307/86; C07D 311/16; C07D 405/04; C07D 493/04; C07D 417/12; C07D 417/14; C07D 491/22; C07D 209/08; C07D 209/18; C07D 209/30; C07D 235/14; C07D 253/18
See application file for complete search history.

(56) References Cited

U.S. PATENT DOCUMENTS

| | | | |
|---|---|---|---|
| 4,522,811 A | 6/1985 | Eppstein et al. |
| 5,134,127 A | 7/1992 | Stella et al. |
| 5,376,645 A | 12/1994 | Stella et al. |
| 5,571,534 A | 11/1996 | Jalonen et al. |
| 5,874,418 A | 2/1999 | Stella et al. |
| 6,046,177 A | 4/2000 | Stella et al. |
| 6,133,248 A | 10/2000 | Stella |
| 6,407,079 B1 | 6/2002 | Muller et al. |

(Continued)

FOREIGN PATENT DOCUMENTS

| | | |
|---|---|---|
| CL | 0501-2003 | 3/2003 |
| CL | 2272-2005 | 9/2005 |

(Continued)

OTHER PUBLICATIONS

Barman Balfour and GOA, "Bendamustine," *Drugs*, 61(5):631-638 (2001).

(Continued)

*Primary Examiner* — Nyeemah A Grazier
*Assistant Examiner* — Amanda L Aguirre
(74) *Attorney, Agent, or Firm* — McCarter & English, LLP; Yu Lu

(57) ABSTRACT

The present invention is directed to pharmaceutical compositions comprising: (a) a cyclopolysaccharide and (b) a compound of Formula (I) or its pharmaceutical acceptable salt:

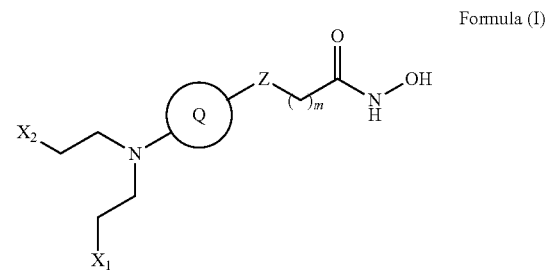

Formula (I)

wherein $X_1$, $X_2$, Q, Z, and m are defined herein. Also disclosed is a method for treating a neoplastic disease or an immune disease with these compositions.

32 Claims, No Drawings

(56) References Cited

U.S. PATENT DOCUMENTS

| | | | |
|---|---|---|---|
| 2006/0079528 A1 | 4/2006 | Finn et al. | |
| 2010/0022512 A1 | 1/2010 | Wisdom et al. | |
| 2010/0216858 A1 | 8/2010 | Popek et al. | |
| 2011/0190363 A1* | 8/2011 | Drager | A61K 9/08 514/394 |
| 2013/0209558 A1* | 8/2013 | Patzak | A61K 39/39558 424/465 |

FOREIGN PATENT DOCUMENTS

| | | | |
|---|---|---|---|
| CL | 3232-2006 | | 11/2006 |
| CN | 101928234 A | * | 12/2010 |
| CN | 102993102 A | * | 3/2013 |
| DE | 34727 A1 | | 12/1964 |
| EP | 0717638 B1 | | 3/2002 |
| WO | WO-2009/100045 A1 | | 8/2009 |
| WO | WO2010/085377 | * | 7/2010 |
| WO | WO-2010/085377 A2 | | 7/2010 |

OTHER PUBLICATIONS

Brewster and Loftsson, "Cyclodextrins as pharmaceutical solubilizers," *Adv. Drug Delivery Rev.*, 59:645-666 (2007).

Chow et al., "In vitro induction of apoptosis of neoplastic cells in low-grade non-Hodgkin's lymphomas using combinations of established cytotoxic drugs with bendamustine," *Haematologica*, 86:485-493 (2001).

Griffith et al., "Novel platinum pyridinehydroxamic acid complexes: synthesis, characterisation, X-ray crystallographic study of nitric oxide related properties," *Polyhedron*, 26:4697-4706 (2007).

Herold et al., "Bop Versus Cop in Advanced Low Grade Non-Hodgin's Lymphomas—Results of a Randomized Multicenter Study," *Blood*, 94(Suppl 1):262a (1999) (Abstract #4382).

Kollmannsberger et al., "Phase II study of bendamustine in patients with relapsed or cisplatin-refractory germ cell cancer," *Anticancer Drugs*, 11:535-539 (2000).

Leoni, "Bendamustine: Rescue of an Effective Antineoplastic Agent From the Mid-Twentieth Century," *Semin Hematol.*, 48 Suppl 1:S4-11 (2011).

Loftsson and Duchêne, "Cyclodextrins and their pharmaceutical applications," *Intl. J. Pharmaceutics*, 329:1-11 (2007).

Minucci and Pelicci, "Histone deacetylase inhibitors and the promise of epigenetic (and more) treatments for cancer," *Nat. Rev. Cancer*, 6:38-51 (2006).

Poenisch et al., "Bendamustine/Prednisone Versus Melphalane/Prednisone in the Primary Treatment of Multiple Myeloma: An Updated Analysis of the 94BP01 Protocol," *Blood*, 96, Suppl 1:759a (2000) (Abstract #3284, Poster Board #-Session: 748-111).

Cai et al., "Solubilization of vorinostat by cyclodextrins," *J. Clin. Pharm. Thera.*, 35:521-526 (2010).

Vyas et al., "Cyclodextrin based novel drug delivery systems," *J. Incl. Phenom. Macrocycl. Chem.*, 62:23-42 (2008).

Pitha et al., "Parenteral hydroxypropyl cyclodextrins: intravenous and intracerebral administration of lipophiles," *J. Pharm. Sci.*, 83(6):833-837 (1994).

Rajewski et al., "Preliminary safety evaluation of parenterally administered sulfoalkyl ether β-cyclodextrin derivatives," *J. Pharm. Sci.*, 84(8):927-932 (1995).

Saulnier et al., "An efficient method for the synthesis of guanidino prodrugs," Bioorganic and Medicinal Chemistry Letters, 4:1985-1990 (1994).

* cited by examiner

PHARMACEUTICAL COMPOSITIONS

RELATED APPLICATIONS

This application is an international application which claims priority to and benefit of U.S. Provisional Application No. 61/536,038, filed on Sep. 18, 2011 and U.S. Provisional Application No. 61/602,408, filed on Feb. 23, 2012. The entire teachings of the above applications are incorporated herein by reference.

BACKGROUND

Cancer is one of the most life threatening diseases in which cells in a part of the body experience out-of-control growth. According to latest data from American Cancer Society, it is estimated to have 1.6 million new cases of cancer in USA in 2011. Cancer is the second leading cause of death in the United States (second only to heart disease) and will claim more than 570,000 lives in 2011. In fact, it is estimated that 50% of all men and 33% of all women living in the United States will develop some type of cancer in their lifetime. Therefore cancer constitutes a major public health burden and represents a significant cost in the United States. For decades, surgery, chemotherapy, and radiation were the established treatments for various cancers. Patients usually receive a combination of these treatments depending upon the type and extent of their disease. But the chemotherapy is most important option for cancer patient when the surgery treatment is impossible.

Bendamustine, a well known chemotherapy first synthesized in 1963, consists of an alkylating nitrogen mustard moiety and a purine-like benzimidazol moiety with a suggested purine-analog effect (Barman Balfour JA, et al, *Drugs* 2001; 61: 631-640). Bendamustine has been shown to have substantial activity against low-grade lymphomas (Herold M, et al., *Blood*, 1999; 94, Suppl 1: 262a), multiple myelomas (Poenisch W, et al., *Blood* 2000; 96, Suppl 1: 759a), and several solid tumors (Kollmannsberger C, et al., *Anticancer Drugs* 2000; 11: 535-539). It was also reported that bendamustine effectively induces apoptosis in lymphoma cells (Chow K U, et al., *Haematologica*, 2001; 86: 485-493). On March 2008, the FDA granted approval to market bendamustine for the treatment of chronic lymphocytic leukemia (CLL). On October 2008, the FDA granted further approval to market bendamustine for the treatment of indolent B-cell non-Hodgkin's lymphoma (NHL) that has progressed during or within six months of treatment with rituximab or a rituximab-containing regimen.

The clinical activity of Bendamustine as a single agent and in combination with other chemotherapeutic and immunotherapeutic drugs, coupled with its potential lack of cross-resistance with many other chemotherapy agents, make bendamustine an attractive therapy for patients with newly diagnosed and refractory hematologic malignancies. [Leoni L M, *Semin Hematol*. 2011 April; 48 Suppl 1:S4-11]. Currently Bendamustine has about 75 active clinical trials for a variety of cancer indications, such as leukemia, lymphoma, small cell lung cancer, multiple myeloma, MDS, ovarian cancer, breast cancer, and brain tumor. Bendamustine, marketed by Cephalon (TREANDA™), has annual sale of $393 million in US in 2010, and an sale of more than $500 million in US in 2011. The peak sale in 2015 may reach 1 billion $. Bendamustine market exclusive right in US will expire in 2015.

Although Bendamustine has made a significant contribution to cancer treatment, the dose-limiting toxicities and drug resistance remain significant hurdles in its clinical use.

In recent years, histone deacetylases (HDAC) has emerged as an important disease target for cancer treatment [Minucci, S. et al., *Nat Rev Cancer* 2006, 6, 38-51]. The human HDAC enzymes have 18 isoforms grouped into Class I-IV according to their sequence homology. Class I, II and IV, commonly referred to as the classical HDACs, are comprised of 11 family members. Class III HDACs consists of 7 enzymes and they are distinct from other HDAC family members, therefore are given a unique term sirtuins. The inhibition of HDAC enzyme leads to histone acetylation which is associated with the remodelling of chromatin and plays a key role in the epigenetic regulation of gene expression. In addition, HDAC inhibitors have been shown to evoke the acetylation of many important non-histone proteins such as HSP90, alpha-tubulin, Ku-70, Bcl-6, importin, cortactin, p53, STAT1, E2F1, GATA-1 and NF-kB, which can alter many important signaling networks related to cancer treatment. The underlying mechanism of action of HDAC inhibitors includes the differentiation, cell cycle arrest, inhibition of DNA repair, induction of apoptosis, upregulation of tumor suppressors, down regulation of growth factors, oxidative stress and autophagy. In the last decade, a large number of structurally diverse HDAC inhibitors have been identified and at least 12 HDAC inhibitors are currently in human clinical trials for cancer treatments, including short-chain fatty acid (valproic acid), hydroxamates (SAHA, LBH589, PXD101, JNJ-26481585, ITF2357, CUDC-101), cyclic tetrapeptides (FK-228), benzamide (MS-275), and several other compounds (CHR-3996, 4SC-201, SB939). Among them, SAHA and FK-228 has been approved by the US FDA for the treatment of advanced cutaneous T-cell lymphoma.

In WO/2010/085377, we reported NL-101, a first-in-class dual-functional Bendamustine derivative which potently inhibits the HDAC pathway. The structure of parental drug Bendamustien and NL-101 is shown below:

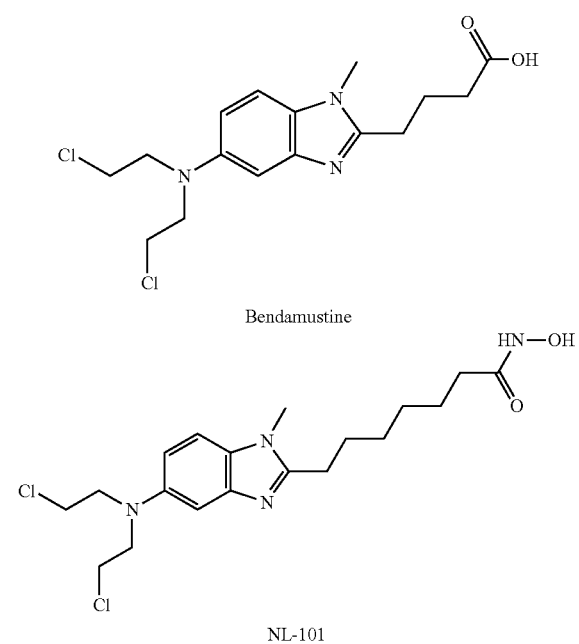

Bendamustine

NL-101

The biological assay showed that NL-101 potently inhibits HDAC enzyme (HDAC1 $IC_{50}$ of 9 nM). NL-101 was sent to NCI (NSC#751447) for NCI-60 cell line panel screening. The data showed that NL-101 is about ×25-100 fold more potent than Bendamustine in the NCI-60 cell lines that are representative of a variety of human cancer type. The sixty $GI_{50}$ values (one for each cell line) make up the fingerprint of the NL-101 and based on this fingerprint, the COMPARE analysis was done by using the COMPARE algorithm on the NCI DTP website. A Pearson correlation coefficient (PCC) of >0.8 indicates >65% agreement in the sensitivity patterns of two compounds and a high likelihood of a common mechanism of action. The COMPARE result showed that the fingerprint of NL-101 did not strongly correlate with any of NSC synthetic compounds (>140,000). In fact, the top match compound is epidoxoform (a doxorubicin derivative) with a PCC of 0.676. Direct comparisons among NL-101, and the conventional nitrogen mustard (e.g. bendamustine, melphalan, and chlorambucil) showed weak correlation coefficients (PCC <0.483). These COMPARE result suggested that NL-101 is not just another conventional nitrogen mustard but possesses unique mechanistic features that differentiate it from the conventional DNA alkylating agents. In another word, NL-101 is expected to be non-cross resistant to the conventional DNA alkylating agents. Therefore NL-101 might have wide potential applications for cancer patients who are resistant, relapse, or refractory to conventional DNA alkylating agents such as bendamustine, melphalan, cisplatin, and temozolomide.

We have developed a first generation formulation of NL-101 for in vivo study, which contains 6 mg/ml NL-101 in buffer system (1.5% acetic acid/0.2% NaOH) with a pH value around 4. The animal study using the first generation formulation of NL-101 shows excellent in vivo efficacy in animal models such as imatinib-resistant Philadelphia chromosome-positive acute lymphoblastic leukemia (Ph+ ALL) model and lung cancer. Ph+ ALL is a leukemia common in adults (~35% of adult ALL) and carries a poor prognosis. Vincristine (VCR), doxorubicin (Dox), cytarabine (AraC), and cyclophosphamde (CTX) are conventional chemotherapy for Ph+ ALL treatment. Our data showed that single dose of NL-101 (60 mpk) has significantly better in vivo efficacy than the bendamustine, SAHA, VCR, Dox, AraC, and CTX (each dosued at MTD) in imatinib-resistant Ph+ ALL model. Weekly dosing of NL-101 at 60 mg/kg has similar efficacy to Sprycel, which is a FDA approved $2^{nd}$ line targeted drug for Ph+ ALL treatment. However, the first generation formulation of NL-101 has unfortunately significant disadvantages, such as low pH value, potential precipitation after injection, and series side effects (e.g, damaged mice tail after iv injection and sometime sudden mice death after quick iv injection due to cardiotoxicity). Therefore, there is a strong need to develop a new generation formulation of NL-101 which can overcome the shortcoming of the first generation formulation, particularly the cardiotoxicity, and can be used in future human clinical trials.

SUMMARY OF THE INVENTION

The present invention relates to a composition comprising (a) a cyclopolysaccharide and (b) a compound of Formula (I), or a pharmaceutically acceptable salt thereof:

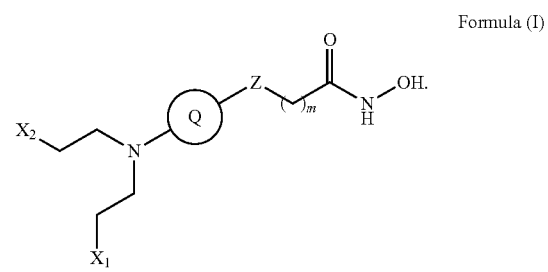

Formula (I)

In Formula I, m is 5, 6, 7, 8, 9, 10, 11, 12, 13, 14, 15, or 16; Z is deleted, $C(R_aR_b)$, O, S, C(O), $N(R_a)$, $SO_2$, OC(O), C(O)O, $OSO_2$, $S(O_2)O$, C(O)S, SC(O), C(O)C(O), $C(O)N(R_a)$, $N(R_a)C(O)$, $S(O_2)N(R_a)$, $N(R_a)S(O_2)$, $OC(O)N(R_a)$, $N(R_a)C(O)O$, $N(R_a)C(O)S$, or $N(R_a)C(O)N(R_b)$, in which each of $R_a$ and $R_b$, independently, is H, alkyl, alkenyl, or alkynyl; $X_1$ and $X_2$ independently, is halo or $OSO_2R_c$, in which $R_c$ is alkyl, alkenyl, or alkynyl; and Q is cycloalkyl, heterocycloalkyl, cycloalkenyl, heterocycloalkenyl, aryl, or heteroaryl, each of which, independently, is optionally substituted with alkyl, alkenyl, alkynyl, cycloalkyl, heterocycloalkyl, cycloalkenyl, heterocycloalkenyl, aryl, heteroaryl, halo, nitro, oxo, —C=NH, cyano, alkyl-$R_d$, $OR_d$, $OC(O)R_d$, $OC(O)OR_d$, $OC(O)SR_d$, $SR_d$, $C(O)R_d$, $C(O)OR_d$, $C(O)SR_d$, $C(O)NR_eR_f$, $SOR_d$, $SO_2R_d$, $NR_eR_f$, or $N(R_e)C(O)R_f$ in which each of $R_d$, $R_e$, and $R_f$ independently, is H, alkyl, alkenyl, alkynyl, cycloalkyl, heterocycloalkyl, aryl, heteroaryl, halo, cyano, amine, nitro, hydroxy, or alkoxy.

One subset of the above-described compounds includes those in which $X_1$ and $X_2$ independently, is halo; Z is deleted, $CH_2$, O, CO, NH, $SO_2$, OC(O), C(O)O, C(O)S, NHC(O), C(O)N11, OC(O)NH, NHC(O)O, or NHC(O)S; m is 5, 6, 7, or 8; and Q is a 9-10 membered aryl or heteroaryl.

One preferred subset of above-described compounds represented by Formula (II)

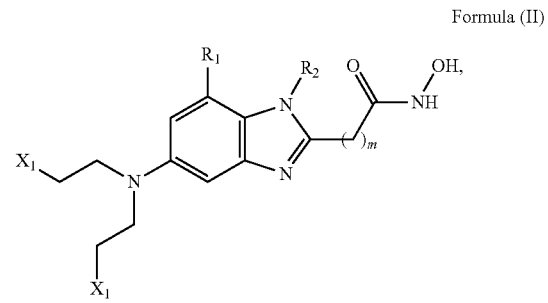

Formula (II)

in which $R_1$ and $R_2$ independently, is H, alkyl, alkenyl, alkynyl, cycloalkyl, heterocycloalkyl, halo, —C=NH, amine, cyano, hydroxy, or alkoxy.

The most preferred compound of above-described compound is represented by Formula (III) (i.e. NL-101):

Formula (III)

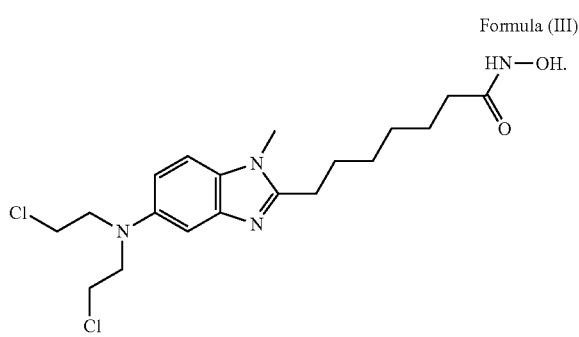 [SMILES: Cn1c(CCCCCCC(=O)NO)nc2cc(N(CCCl)CCCl)ccc21]

In another aspect, a preferred pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, biocarbonate, carbonate, sodium hydroxide salt, calcium hydroxide salt, potassium hydroxide salt, tromethamine salt, or mixtures thereof. A more preferred pharmaceutically acceptable salt is a hydrochloride salt, methanesulfonate, toluenesulfonate, acetate, succinate, citrate, maleate, tartrate, or mixtures thereof. The most preferred pharmaceutically acceptable salt is an acetate salt.

In another aspect, a preferred cyclopolysaccharide is α-cyclodextrin or a derivative thereof, β-cyclodextrin or derivative thereof, and γ-cyclodextrin or a derivative thereof. A more preferred cyclopolysaccharide is β-cyclodextrin or derivative thereof. The most preferred cyclopolysaccharide is hydroxypropyl β-cyclodextrin, or sulfobutylether β-cyclodextrin.

As shown below in Example 6, we are surprised to found that composition comprising NL-101 and hydroxypropyl β-cyclodextrin can significantly reduce the cardiotoxicity in vivo. Furthermore, as shown below in Example 10, in a NSCLC xengoraft A549 model, animals treated with a composition comprising NL-101 and hydroxypropyl β-cyclodextrin showed significantly decreased tumor size compared with animals treated with the parental drug Bendamustine and the vehicle group.

The compositions of the present invention are useful in treating a patient having a tumor. The compounds of the invention may also useful in the prevention and treatment of an immune disease.

This invention also relates to a method of treating a neoplastic disorder (e.g., cancer, myelodysplastic syndrome, or myeloproliferative disease) by administering to a subject in need thereof an effective amount of compositions thereof described above.

Furthermore, this invention relates to a method of treating an immune disease (e.g., rheumatoid arthritis and multiple sclerosis) by administering to a subject in need thereof an effective amount of compositions thereof described above.

The details of one or more embodiments of the invention are set forth in the description below. Other features, objects, and advantages of the invention will be apparent from the description and from the claims.

DETAILED DESCRIPTION

In a first embodiment, the invention is a composition comprising (a) cyclopolysaccharide, and (b) a compound of Formula (I) illustrated above, or its geometric isomers, enantiomers, diastereomers, racemates, pharmaceutically acceptable salts, prodrugs and solvates thereof.

In a preferred embodiment, the invention is a composition comprising (a) cyclopolysaccharide, and (b) a compound of Formula (II) illustrated above, or its geometric isomers, enantiomers, diastereomers, racemates, pharmaceutically acceptable salts, prodrugs and solvates thereof.

In a most preferred embodiment, the invention is a composition comprising (a) cyclopolysaccharide, and (b) a compound of Formula (III) illustrated above, or its geometric isomers, enantiomers, diastereomers, racemates, pharmaceutically acceptable salts, prodrugs and solvates thereof.

Exemplary compounds described herein include, but are not limited, to the following:

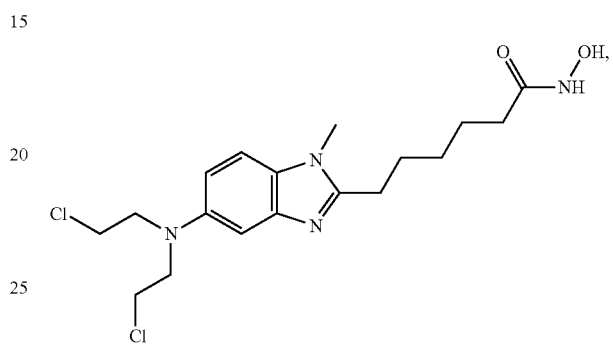

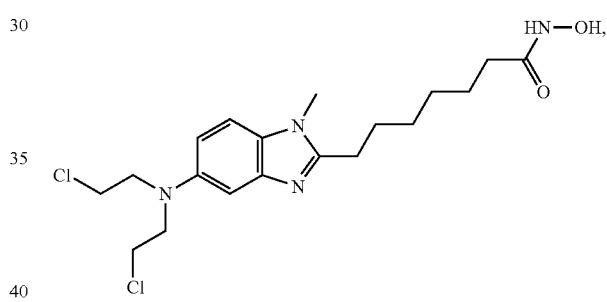

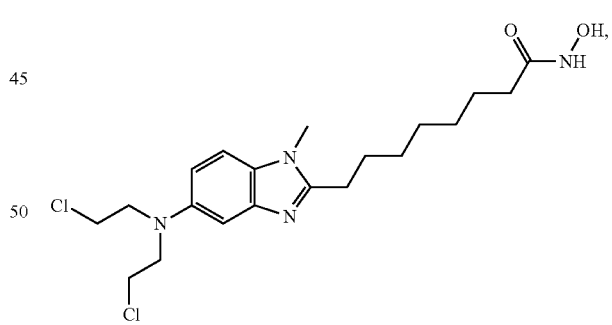

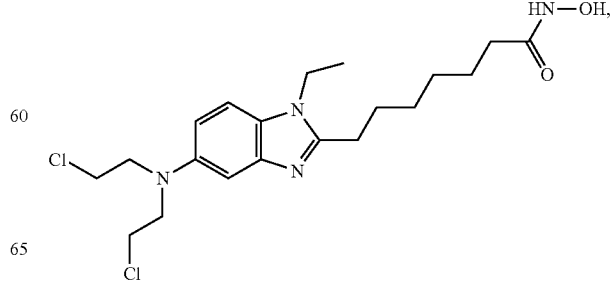

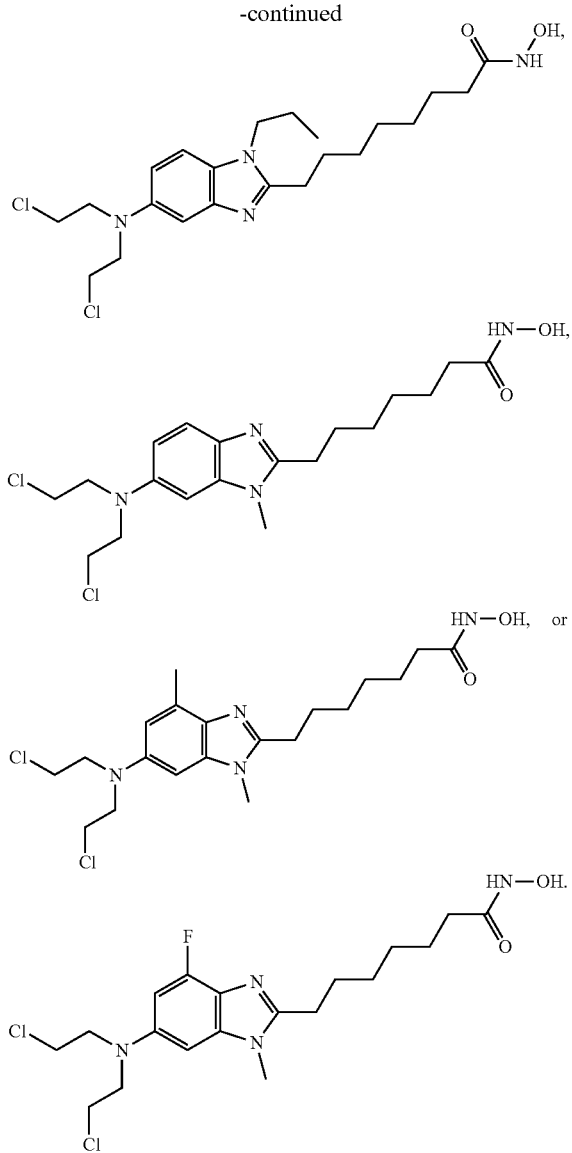

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

It should be recognized that the compounds of the present invention may be present and optionally administered in the form of salts, solvates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen-containing groups may be quaternized with such agents as ($C_{1-4}$) alkyl halides, e.g., methyl, ethyl, iso-propyl and tert-butyl chlorides, bromides and iodides; di-($C_{1-4}$) alkyl sulfates, e.g., dimethyl, diethyl and diamyl sulfates; alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water-soluble and oil-soluble compounds of the present invention.

Compounds of the present invention that comprise a tertiary nitrogen atoms may be oxidized by such agents as hydrogen peroxide ($H_2O_2$), Caro's acid or peracids like meta-Chloroperoxybenzoic acid (mCPBA) to from amine oxide. Amine oxides of anti-cancer agents have been developed as prodrugs and may be water-soluble.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), Bioorganic and Medicinal Chemistry Letters, Vol. 4, p. 1985.

Cyclopolysaccharides: the cyclopolysaccharides which may employed in the practice of this invention include cyclodextrins, cyclomannins, cycloaltrins, cyclofructins and the like. In general, cyclopolysaccharides comprising between 6 and 8 sugar units are preferred. Among the preferred cyclopolysaccharides which may be employed are cyclodextrins.

Cyclodextrins are cyclic oligomers of dextrose with a truncated cone structure consisting of a hydrophilic exterior and a hydrophobic interior cavity. A cyclodextrin can form an inclusion complex with a guest molecule by complexing with all or a portion of a hydrophobic guest molecule within its cavity. The size of the cavity is determined by the number of glucopyranose units in the cyclodextrin. Alpha-(α), beta-(β), and gamma-(γ) cyclodextrins are the most common cyclodextrins and possess six, seven and eight glucopyranose units, respectively. Because natural cyclodextrins have relatively low aqueous solubility and are associated with toxicity, chemically modified cyclodextrin derivatives have been developed to overcome these limitations. Such cyclodextrin derivatives typically possess a chemical modification at one or more of the 2, 3, or 6 position hydroxyl groups. Cyclodextrin derivatives have, for example, been described in U.S. Pat. Nos. 5,134,127; 5,376,645; 5,571,534; 5,874,418; 6,046,177 and 6,133,248, the contents of which are herein incorporated by reference and made a part hereof. As used herein, the terms "cyclodextrin," "α-cyclodextrin," β-cyclodextrin and "γ-cyclodextrin" are intended to encompass unmodified cyclodextrins as well as chemically modified derivatives thereof. The compositions of the invention comprise an inclusion complex of a cyclodextrin and a compound of Formulae (I), (II), or (III).

In yet another embodiment, the composition comprises a therapeutically-effective concentration of a compound of Formulae (I), (II), or (III).

In one embodiment of the invention, the composition comprises a cyclodextrin selected from the group consisting of α-cyclodextrin, β-cyclodextrin and γ-cyclodextrin.

In yet another embodiment, the cyclodextrin is a β-cyclodextrin and γ-cyclodextrin.

In an additional embodiment, the cyclodextrin is a β-cyclodextrin.

In a further embodiment, the cyclodextrin is selected from the group consisting of a hydroxypropyl-β-cyclodextrin (Pitha et al, J Pharm Sci, 84 (8), 927-32 (1995)) and sulfobutyl derivatized-β-cyclodextrin (described, for example, in U.S. Pat. Nos. 5,134,127; 5,376, 645; 5,874,418; 6,046,177 and 6,133,248).

In another embodiment, the cyclodextrin is a hydroxypropyl β-cyclodextrin.

In yet another embodiment of the invention, the cyclodextrin is sulfobutylether-β-cyclodextrin.

Other preferred cyclopolysaccharides include, but are not limited to, β-cyclodextrin substituted with 2-hydroxy-N,N, N-trimethylpropanammonium, carboxymethylated-β-cyclodextrin, O-phosphated-β-cyclodextrin, succinyl-(2-hydroxyl)propyl-betacyclodextrin, sulfopropylated-β-cyclodextrin, heptakis(6amino-6-deoxy)-β-cyclodextrin, O-sulfated-β-cyclodextrin, and 6-monodeoxy-6-mono(3-hydroxy)propylamino-β-cyclodextrin;

The cyclodextrin may be included in an amount that increases the solubility of the active compound in the composition. In one embodiment, the amount of cyclodextrin included within the composition is the minimal amount needed to solubilize the drug in the composition. In a further embodiment, the composition is a parenteral formulation and the amount of cyclodextrin included within the formulation is the minimal amount of cyclodextrin needed to solubilize the drug.

In order to determine the minimum amount of cyclodextrin needed to solubilize a compound encompassed by Formulae I-III, a plot of the compound's solubility versus cyclodextrin concentration can be carried out. By interpolating or extrapolating from the plot, a composition can be prepared that contains the minimum amount of cyclodextrin needed to dissolve the desired concentration of the active compound.

In one embodiment, the composition comprises at least 2.5% (weight/volume) of a cyclodextrin. In another embodiment, the composition comprises at least 5% of a cyclodextrin. In yet another embodiment, the composition comprises at least 10% of a cyclodextrin. In a further embodiment, the composition comprises from 2.5 to 40% of a cyclodextrin. In yet another embodiment, the composition comprises from 5% to 20% of a cyclodextrin. In another embodiment, the composition comprises 7.5% to 15% of a cyclodextrin. In yet another embodiment, the composition comprises about 10% of a cyclodextrin.

In one embodiment, the composition comprises at least 2.5% (weight/volume) of a β-cyclodextrin. In another embodiment, the composition comprises at least 5% of a cyclodextrin. In yet another embodiment, the composition comprises at least 10% of a β-cyclodextrin. In a further embodiment, the composition comprises from 2.5 to 40% of a β-cyclodextrin. In yet another embodiment, the composition comprises from 5% to 20% of a β-cyclodextrin. In another embodiment, the composition comprises 7.5% to 15% of a β-cyclodextrin. In yet another embodiment, the composition comprises 10% of a β-cyclodextrin.

In one embodiment, the composition comprises at least 2.5% (weight/volume) of a hydroxypropyl β-cyclodextrin or sulfobutylether β-cyclodextrin. In another embodiment, the composition comprises at least 5% of a hydroxypropyl β-cyclodextrin or sulfobutylether β-cyclodextrin. In yet another embodiment, the composition comprises at least 10% of a hydroxypropyl β-cyclodextrin or sulfobutylether β-cyclodextrin. In a further embodiment, the composition comprises from 2.5 to 40% of a hydroxypropyl β-cyclodextrin or sulfobutylether β-cyclodextrin. In yet another embodiment, the composition comprises from 5% to 20% of a hydroxypropyl β-cyclodextrin or sulfobutylether β-cyclodextrin. In another embodiment, the composition comprises 7.5% to 15% of a hydroxypropyl β-cyclodextrin or sulfobutylether β-cyclodextrin. In yet another embodiment, the composition comprises 10% of a hydroxypropyl β-cyclodextrin or sulfobutylether β-cyclodextrin.

In one embodiment, the composition further comprises pH adjusting agents. In a further embodiment, the pH adjusting agents are one or more acids, bases, or salts. Examples of acids that may be included in the composition include inorganic acids such as hydrochloric acid, sulfuric acid, phosphoric acid, or mixtures thereof, and organic acids such as citric acid, L(−)-malic acid and L(+)tartaric, acid or mixtures thereof. Examples of bases that may be included in the composition include sodium hydroxide, potassium hydroxide, calcium hydroxide, tromethamine, or mixtures thereof. Examples of salt that may be included in the composition include sodium bicarbonate, sodium carbonate, sodium citrate, or mixtures thereof. In a further embodiment, the composition comprising one or more pH adjusting agents has a pH range of 6.0-9.0, preferably 7.0-8.0.

Another embodiment of the invention is a pharmaceutical dosage form that includes a pharmaceutical composition containing 5 to about 500 mg of compound of Formula (I-III). The more preferred formula is Formula (II), and the most preferred formula is Formula (III).

In a further embodiment, the composition comprises dextran. In yet another embodiment, the composition comprises dextran in an amount of range from about 1% to about 5% weight/volume dextran. In a further embodiment, the composition comprises from about 2 to about 4% weight/volume dextran.

Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The composition of the invention may be prepared by mixing a solution of the cyclopolysaccharide with an stock solution of a compound of Formula (I). Such resulting mixture is vigorously mixed and optionally subjected to the action of ultrasound waves to obtain a homogenous and equilibrated aqueous solution. Preferably, the final composition is filtered before use for injection. The composition may be optionally freeze-dried to produce a solid material suitable for dissolution in injection media before its use.

DEFINITIONS

"Acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Aliphatic" means a moiety characterized by a straight or branched chain arrangement of constituent carbon atoms and may be saturated or partially unsaturated with one or more double or triple bonds.

The term "alkyl" refers to a straight or branched hydrocarbon containing 1-20 carbon atoms (e.g., $C_1$-$C_{10}$). Examples of alkyl include, but are not limited to, methyl, methylene, ethyl, ethylene, n-propyl, n-butyl, i-butyl, and t-butyl. The term "alkenyl" refers to a straight or branched hydrocarbon containing 2-20 carbon atoms (e.g., $C_2$-$C_{10}$) and one or more double bonds. Examples of alkenyl include, but are not limited to, ethenyl, propenyl, and allyl. The term "alkynyl" refers to a straight or branched hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl. "Alkoxy" means an oxygen moiety having a further alkyl substituent. "Alkoxycarbonyl" means an alkoxy group attached to a carbonyl group. "Oxoalkyl" means an alkyl, further substituted with a carbonyl group. The carbonyl group may be an aldehyde, ketone, ester, amide, acid or acid chloride.

The term "cycloalkyl" refers to a saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 30 carbons (e.g., $C_3$-$C_{12}$) and one or more double bonds. Examples include cyclopentenyl, cyclohexenyl, and cycloheptenyl. The term "heterocycloalkyl" refers to a nonaromatic 5-8 membered monocyclic, 8-12 membered bicyclic, or 11-14 membered tricyclic ring system having one or more heteroatoms (such as O, N, S, P, or Se). Examples of heterocycloalkyl groups include, but are not limited to, piperazinyl, pyrrolidinyl, dioxanyl, morpholinyl, and tetrahydrofuranyl. The term "heterocycloalkenyl" refers to a nonaromatic 5-8 membered monocyclic, 8-12 membered bicyclic, or 11-14 membered tricyclic ring system having one or more heteroatoms (such as O, N, S, P, or Se) and one or more double bonds.

The term "aryl" refers to a 6-carbon monocyclic, 10-carbon bicyclic, 14-carbon' tricyclic aromatic ring system. Examples of aryl groups include, but are not limited to, phenyl, naphthyl, and anthracenyl. The term "heteroaryl" refers to an aromatic 5-8 membered monocyclic, 8-12 membered bicyclic, or 11-14 membered tricyclic ring system having one or more heteroatoms (such as O, N, S, P, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, alkylamino, aryl, and heteroaryl mentioned above include both substituted and unsubstituted moieties. Possible substituents on alkylamino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aromatic" means a moiety wherein the constituent atoms make up an unsaturated ring system, all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Carbamoyl" means the radical —OC(O)NRaRb where Ra and Rb are each independently two further substituents where a hydrogen or carbon atom is alpha to the nitrogen. It is noted that carbamoyl moieties may include protected derivatives thereof. Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Halo" means fluoro, chloro, bromo or iodo.

"Halo-substituted alkyl", as an isolated group or part of a larger group, means "alkyl" substituted by one or more "halo" atoms, as such terms are defined in this application. Halo-substituted alkyl includes haloalkyl, dihaloalkyl, trihaloalkyl, perhaloalkyl and the like.

"Hydroxy" means the radical —OH.

"Imine derivative" means a derivative comprising the moiety —C(NR)—, wherein R comprises a hydrogen or carbon atom alpha to the nitrogen.

"Isomers" mean any compound having identical molecular formulae but differing in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality. A mixture of the two enantiomeric forms is termed a "racemic mixture".

"Nitro" means the radical —$NO_2$.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, Protecting Groups in Organic Synthesis, 3rd edition, John Wiley & Sons, 1999.

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety.

"Sulfide" means —S—R wherein R is II, alkyl, carbocycle, heterocycle, carbocycloalkyl or heterocycloalkyl. Particular sulfide groups are mercapto, alkylsulfide, for example methylsulfide (—S-Me); arylsulfide, for example phenylsulfide; aralkylsulfide, for example benzylsulfide.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Thiocarbonyl" means the radical —C(S)—. It is noted that the thiocarbonyl radical' may be further substituted with a variety of substituents to form different thiocarbonyl groups including thioacids, thioamides, thioesters, and thioketones.

"Animal" includes humans, non-human mammals (e.g., dogs, cats, rabbits, cattle, horses, sheep, goats, swine, deer, and the like) and non-mammals (e.g., birds, and the like).

"Bioavailability" as used herein is the fraction or percentage of an administered dose of a drug or pharmaceutical composition that reaches the systemic circulation intact. In general, when a medication is administered intravenously, its bioavailability is 100%. However, when a medication is administered via other routes (e.g., orally), its bioavailability decreases (e.g., due to incomplete absorption and first-pass metabolism). Methods to improve the bioavailability include prodrug approach, salt synthesis, particle size reduction, complexation, change in physical form, solid dispersions, spray drying, and hot-melt extrusion.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases.

"Prodrug" means a compound that is convertible in vivo metabolically into an inhibitor according to the present invention. For example, an inhibitor comprising a hydroxyl group may be administered as an ester that is converted by hydrolysis in vivo to the hydroxyl compound.

"Pharmacophore", as defined by The International Union of Pure and Applied Chemistry, is an ensemble of steric and electronic features that is necessary to ensure the optimal supramolecular interactions with a specific biological target and to trigger (or block) its biological response. For example, Camptothecin is the pharmacophore of the well known drug topotecan and irinotecan. As another example, nitrogen mustard pharmacophore has a typical formula of —N(CH$_2$CH$_2$X)$_2$ or its N-oxide analogues in which X is a leaving group such as halo. The anti-cancer drugs containing a nitrogen mustard pharmacophore include but not limited to Melphalan, Bendamustine, Cyclophosphamide, PX-478, TH-302, PR-104, Ifofamide, and so on.

"Pharmaceutically acceptable carrier" means a non-toxic solvent, dispersant, excipient, adjuvant, or other material which is mixed with the compound of the present invention in order to permit the formation of a pharmaceutical composition, i.e, a dose form capable of administration to the patient. Examples of pharmaceutically acceptable carrier includes suitable polyethylene glycol (e.g PEG400), surfactant (e.g Cremophor), or cyclopolysaccharide (e.g hydroxypropyl-β-cyclodextrin or sulfobutyl ether β-cyclodextrins), polymer, liposome, micelle, nanosphere, and so on.

"Stability" in general refers to the length of time a drug retains its properties without loss of potency. Sometimes this is referred to as shelf life. Factors affecting drug stability include, among other things, the chemical, structure of the drug, impurity in the formulation, pH, moisture content, as well as environmental factors such as temperature, oxidization, light, and relative humidity. Stability can be improved by providing suitable chemical and/or crystal modifications (e.g., surface modifications that can change hydration kinetics; different crystals that can have different properties), excipients (e.g., anything other than the active substance in the dosage form), packaging conditions, storage conditions, etc.

"Therapeutically effective amount" of a composition described herein is meant an amount of the composition which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the composition described above may range from about 0.1 mg/kg to about 500 mg/Kg, preferably from about 0.2 to about 50 mg/kg. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

As used herein, the term "treating" refers to administering a compound to a subject that has a neoplastic or immune disorder, or has a symptom of or a predisposition toward it, with the purpose to cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents. A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

General

"Combination therapy" includes the administration of the subject compositions of the present invention in further combination with other biologically active ingredients (such as, but not limited to, a second and different antineoplastic agent) and non-drug therapies (such as, but not limited to, surgery or radiation treatment). For instance, the compositions of the invention can be used in combination with other pharmaceutically active compounds, or non-drug therapies, preferably compounds that are able to enhance the effect of the compositions of the invention. The compositions of the invention can be administered simultaneously (as a single preparation or separate preparation) or sequentially to the other therapies. In general, a combination therapy envisions administration of two or more drugs/treatments during a single cycle or course of therapy.

In one embodiment, the compositions of the invention are administered in combination with one or more of traditional chemotherapeutic agents. The traditional chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as Nitrosureas (e.g., Carmustine, Lomustine and Streptozocin), ethylenimines (e.g., thiotepa, hexamethylmelanine), Alkylsulfonates (e.g., Busulfan), Hydrazines and Triazines (e.g., Altretamine, Procarbazine, Dacarbazine and Temozolomide), and platinum based agents (e.g., Carboplatin, Cisplatin, and Oxaliplatin); plant alkaloids such as Podophyllotoxins (e.g., Etoposide and Tenisopide), Taxanes (e.g., Paclitaxel and Docetaxel), Vinca alkaloids (e.g., Vincristine, Vinblastine and Vinorelbine); anti-tumor antibiotics such as Chromomycins (e.g., Dactinomycin and Plicamycin), Anthracyclines (e.g., Doxorubicin, Daunorubicin, Epirubicin, Mitoxantrone, and Idarubicin), and miscellaneous antibiotics such as Mitomycin and Bleomycin; anti-metabolites such as folic acid antagonists (e.g., Methotrexate), pyrimidine antagonists (e.g., 5-Fluorouracil, Foxuridine, Cytarabine, Capecitabine, and Gemcitabine), purine antagonists (e.g., 6-Mercaptopurine and 6-Thioguanine) and adenosine deaminase inhibitors (e.g., Cladribine, Fludarabine, Nelarabine and Pentostatin); topoisomerase inhibitors such as topoisomerase I inhibitors (Topotecan, Irinotecan), topoisomerase II inhibitors (e.g., Amsacrine, Etoposide, Etoposide phosphate, Teniposide), and miscellaneous anti-neoplastics such as ribonucleotide reductase inhibitors (Hydroxyurea), adrenocortical steroid inhibitor (Mitotane), anti-microtubule agents (Estramustine), and retinoids (Bexarotene, Isotretinoin, Tretinoin (ATRA).

In one aspect of the invention, the compositions may be administered in combination with one or more targeted anti-cancer agents that modulate protein kinases involved in various disease states. Examples of such kinases may include, but are not limited ABL1, ABL2/ARG, ACK1, AKT1, AKT2, AKT3, ALK, ALK1/ACVRL1, ALK2/ACVR1, ALK4/ACVR1B, ALK5/TGFBR1, ALK6/BMPR1B, AMPK(A1/B1/G1), AMPK(A1/B1/G2), AMPK(A1/B1/G3), AMPK (A1/B2/G1), AMPK(A2/B1/G1), AMPK(A2/B2/G1), AMPK(A2/B2/G2), ARAF, ARK5/NUAK1, ASK1/MAP3K5, ATM, Aurora A, Aurora B, Aurora C, AXL, BLK, BMPR2, BMX/ETK, BRAF, BRK, BRSK1, BRSK2, BTK, CAMK1a, CAMK1b, CAMK1d, CAMK1g, CAMKIIa, CAMKIIb, CAMKIId, CAMKIIg, CAMK4, CAMKK1, CAMKK2, CDC7-DBF4, CDK1-cyclin A, CDK1-cyclin B, CDK1-cyclin E, CDK2-cyclin A, CDK2-cyclin A1, CDK2-cyclin E, CDK3-cyclin E, CDK4-cyclin D1, CDK4-cyclin D3, CDK5-p25, CDK5-p35, CDK6-cyclin D1, CDK6-cyclin D3, CDK7-cyclin H, CDK9-cyclin K, CDK9-cyclin T1, CHK1, CHK2, CK1a1, CK1d, CK1 epsilon, CK1g1, CK1g2, CK1g3, CK2a, CK2a2, c-KIT, CLK1, CLK2, CLK3, CLK4, c-MER, c-MET, COT1/MAP3K8, CSK, c-SRC, CTK/MATK, DAPK1, DAPK2, DCAMKL1, DCAMKL2, DDR1, DDR2, DLK/MAP3K12, DMPK, DMPK2/CDC42BPG, DNA-PK, DRAK1/STK17A, DYRK1/DYRK1A, DYRK1B, DYRK2, DYRK3, DYRK4, EEF2K, EGFR, EIF2AK1, EIF2AK2, EIF2AK3, EIF2AK4/GCN2, EPHA1, EPHA2, EPHA3, EPHA4, EPHA5, EPHA6, EPHA7, EPHA8, EPHB1, EPHB2, EPHB3, EPHB4, ERBB2/HER2, ERBB4/HER4, ERK1/MAPK3, ERK2/MAPK1, ERK5/MAPK7, FAK/PTK2, FER, FES/FPS, FGFR1, FGFR2, FGFR3, FGFR4, FGR, FLT1/VEGFR1, FLT3, FLT4/VEGFR3, FMS, FRK/PTK5, FYN, GCK/MAP4K2, GRK1, GRK2, GRK3, GRK4, GRK5, GRK6, GRK7, GSK3a, GSK3b, Haspin, HCK, HGK/MAP4K4, HIPK1, HIPK2, HIPK3, HIPK4, HPK1/MAP4K1, IGF1R, IKKa/CHUK, IKKb/IKBKB, IKKe/IKBKE, IR, IRAK1, IRAK4, IRR/INSRR, ITK, JAK1, JAK2, JAK3, JNK1, JNK2, JNK3, KDR/VEGFR2, KHS/MAP4K5, LATS1, LATS2, LCK, LCK2/ICK, LKB1, LIMK1, LOK/STK10, LRRK2, LYN, LYNB, MAPKAPK2, MAPKAPK3, MAPKAPK5/PRAK, MARK1, MARK2/PAR-1Ba, MARK3, MARK4, MEK1, MEK2, MEKK1, MEKK2, MEKK3, MELK, MINK/MINK1, MKK4, MKK6, MLCK/MYLK, MLCK2/MYLK2, MLK1/MAP3K9, MLK2/MAP3K10, MLK3/MAP3K11, MNK1, MNK2, MRCKa/, CDC42BPA, MRCKb/, CDC42BPB, MSK1/RPS6KA5, MSK2/RPS6KA4, MSSK1/STK23, MST1/STK4, MST2/STK3, MST3/STK24, MST4, mTOR/FRAP1, MUSK, MYLK3, MYO3b, NEK1, NEK2, NEK3, NEK4, NEK6, NEK7, NEK9, NEK11, NIK/MAP3K14, NLK, OSR1/OXSR1, P38a/MAPK14, P38b/MAPK11, P38d/MAPK13, P38g/MAPK12, P70S6K/RPS6 KB1, p70S6Kb/, RPS6KB2, PAK1, PAK2, PAK3, PAK4, PAK5, PAK6, PASK, PBK/TOPK, PDGFRa, PDGFRb, PDK1/PDPK1, PDK1/PDHK1, PDK2/PDHK2, PDK3/PDHK3, PDK4/PDHK4, PHKg1, PHKg2, PI3Ka, (p110a/p85a), PI3Kb, (p110b/p85a), PI3Kd, (p110d/p85a), PI3Kg(p120g), PIM1, PIM2, PIM3, PICA, PKAcb, PKAcg, PKCa, PKCb1, PKCb2, PKCd, PKCepsilon, PKCeta, PKCg, PKCiota, PKCmu/PRKD1, PKCnu/PRKD3, PKCtheta, PKCzeta, PKD2/PRKD2, PKG1a, PKG1b, PKG2/PRKG2, PKN1/PRK1, PKN2/PRK2, PKN3/PRK3, PLK1, PLK2, PLK3, PLK4/SAK, PRKX; PYK2, RAFT, RET, RIPK2, RIPK3, RIPK5, ROCK1, ROCK2, RON/MST1R, ROS/ROS1, RSK1, RSK2, RSK3, RSK4, SGK1, SGK2, SGK3/SGKL, SIK1, SIK2, SLK/STK2, SNARK/NUAK2, SRMS, SSTK/TSSK6, STK16, STK22D/TSSK1, STK25/YSK1, STK32b/YANK2, STK32c/YANK3, STK33, STK38/NDR1, STK38L/NDR2, STK39/STLK3, SRPK1, SRPK2, SYK, TAK1, TAOK1, TAOK2/TAO1, TAOK3/JIK, TBK1, TEC, TESK1, TGFBR2, TIE2/TEK, TLK1, TLK2, TNIK, TNK1, TRKA, TRKB, TRKC, TRPM7/CHAK1, TSSK2, TSSK3/STK22C, TTBK1, TTBK2, TTK, TXK, TYK1/LTK, TYK2, TYRO3/SKY, ULK1, ULK2, ULK3, VRK1, VRK2, WEE1, WNK1, WNK2, WNK3, YES/YES1, ZAK/MLTK, ZAP70, ZIPK/DAPK3, KINASE, MUTANTS, ABL1(E255K), ABL1(F317I), ABL1(G250E), ABL1(H396P), ABL1 (M351T), ABL1(Q252H), ABL1(T315I), ABL1(Y253F), ALK (C1156Y), ALK(L1196M), ALK (F1174L), ALK (R1275Q), BRAF(V599E), BTK(E41K), CHK2(I157T), c-Kit(A829P), c-KIT(D816H), c-KIT(D816V), c-Kit (D820E), c-Kit(N822K), C-Kit (T670I), c-Kit(V559D), c-Kit(V559D/V654A), c-Kit(V559D/T670I), C-Kit (V560G), c-KIT(V654A), C-MET(D1228H), C-MET (D1228N), C-MET(F12001), c-MET(M1250T), C-MET (Y1230A), C-MET(Y1230C), C-MET(Y1230D), C-MET (Y1230H), c-Src(T341M), EGFR(G719C), EGFR(G719S), EGFR(L858R), EGFR(L861Q), EGFR(T790M), EGFR, (L858R,T790M), EGFR(d746-75011790M), EGFR(d746-750), EGFR(d747-749/A750P), EGFR(d747-7521P753S), EGFR(d752-759), FGFR1(V561M), FGFR2(N549H), FGFR3(G697C), FGFR3(K650E), FGFR3(K650M), FGFR4(N535K), FGFR4(V550E), FGFR4(V550L), FLT3 (D835Y), FLT3(1TD), JAK2 (V617F), LRRK2 (G2019S), LRRK2 (I2020T), LRRK2 (R1441C), p38a(T106M), PDG-FRa(D842V), PDGFRa(T6741), PDGFRa(V56 ID), RET (E762Q), RET(G691S), RET(M918T), RET(R749T), RET (R813Q), RET(V804L), RET(V804M), RET(Y791F), TIF2 (R849W), TIF2(Y897S), and TIF2(Y1108F).

In another aspect of the invention, the subject compositions may be administered in combination with one or more targeted anti-cancer agents that modulate non-kinase biological targets, pathway, or processes. Such targets pathways, or processes include but not limited to heat shock proteins (e.g. HSP90), poly-ADP (adenosine diphosphate)-ribose polymerase (PARP), hypoxia-inducible factors (HIF), proteasome, Wnt/Hedgehog/Notch signaling proteins, TNF-alpha, matrix metalloproteinase, farnesyl transferase, apoptosis pathway (e.g Bcl-xL, Bcl-2, Bcl-w), histone deacetylases (HDAC), histone acetyltransferases (HAT), and methyltransferase (e.g histone lysine methyltransferases, histone arginine methyltransferase, DNA methyltransferase, etc).

In another aspect of the invention, the compositions of the invention are administered in combination with one or more of other anti-cancer agents that include, but are not limited to, hormonal therapies (e.g Tamoxifen, Fulvestrant, Clomifene, Anastrozole, Exemestane, Formestane, Letrozole, etc), vascular disrupting agent, gene therapy, RNAi cancer therapy, chemoprotective agents (e.g., amfostine, mesna, and dexrazoxane), antibody conjugate(e.g brentuximab vedotin, ibritumomab tiuxetan), cancer immunotherapy such as Interleukin-2, cancer vaccines (e.g., sipuleucel-T) or monoclonal antibodies (e.g., Bevacizumab, Alemtuzumab, Rituximab, Trastuzumab, etc).

In another aspect of the invention, the subject compositions are administered in combination with radiation therapy or surgeries. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain preferred embodiments, the compositions of the invention are administered in combination with one or more of radiation therapy, surgery, or anti-cancer agents that include, but are not limited to, DNA damaging agents, antimetabolites, topoisomerase inhibitors, anti-microtubule agents, EGFR inhibitors, HER2 inhibitors, VEGFR2 inhibitors, BRAF inhibitors, Bcr-Abl inhibitors, PDGFR inhibitors, ALK inhibitors, PLK inhibitors, MET inhibitors, epigenetic agents, HSP90 inhibitors, PARP inhibitors, CHK inhibitors, aromatase inhibitor, estrogen receptor antagonist, and antibodies targeting VEGF, HER2, EGFR, CD50, CD20, CD30, CD33, etc.

In certain preferred embodiments, the compositions of the invention are administered in combination with one or more of abarelix, abiraterone acetate, aldesleukin, alemtuzumab, altretamine, anastrozole, asparaginase, bevacizumab, bexarotene, bicalutamide, bleomycin, bortezombi, brentuximab vedotin, busulfan, capecitabine, carboplatin, carmustine, cetuximab, chlorambucil, cisplatin, cladribine, clofarabine; clomifene, crizotinib, cyclophosphamide, dasatinib, daunorubicin liposomal, decitabine, degarelix, denileukin diftitox, denileukin diftitox, denosumab, docetaxel, doxorubicin, doxorubicin liposomal, epirubicin, eribulin mesylate, erlotinib, estramustine, etoposide phosphate, everolimus, exemestane, fludarabine, fluorouracil, fotemustine, fulvestrant, gefitinib, gemcitabine, gemtuzumab ozogamicin, goserelin acetate, histrelin acetate, hydroxyurea, ibritumomab tiuxetan, idarubicin, Ifosfamide, imatinib mesylate, interferon alfa 2a, ipilimumab, ixabepilone, lapatinib ditosylate, lenalidomide, letrozole, leucovorin, leuprolide acetate, levamisole, lomustine, mechlorethamine, melphalan, methotrexate, mitomycin C, mitoxantrone, nelarabine, nilotinib, oxaliplatin, paclitaxel, paclitaxel protein-bound particle, pamidronate, panitumumab, pegaspargase, peginterferon alfa-2b, pemetrexed disodium, pentostatin, raloxifene, rituximab, sorafenib, streptozocin, sunitinib maleate, tamoxifen, temsirolimus, teniposide, thalidomide, toremifene, tositumomab, trastuzumab, tretinoin, uramustine, vandetanib, vemurafenib, vinorelbine, zoledronate, radiation therapy, or surgery.

A wide variety of administration methods may be used in conjunction with the compositions of the present invention. Compositions of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions according to the invention may also be administered or coadministered in slow release dosage forms. Compositions may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used.

The invention further provides methods for the prevention or treatment of a neoplastic disease or immune disease. In one embodiment, the invention relates to a method of treating a neoplastic disease or immune disease in a subject in need of treatment comprising administering to said subject a therapeutically effective amount of a composition of the invention. In one embodiment, the invention further provides for the use of a composition of the invention in the manufacture of a medicament for halting or decreasing a neoplastic disease or immune disease.

The neoplastic disease includes but not limited to lung cancer, head and neck cancer, central nervous system cancer, prostate cancer, testicular cancer, colorectal cancer, pancreatic cancer, liver cancer, stomach cancer, biliary tract cancer, esophageal cancer, gastrointestinal stromal tumor, breast cancer, cervical cancer, ovarian cancer, uterine cancer, leukemia, lymphomas, multiple myeloma, melanoma, basal cell carcinoma, squamous cell carcinoma, bladder cancer, renal cancer, sarcoma, mesothelioma, thymoma, myelodysplastic syndrome and myeloproliferative disease.

It is well known that immunosuppression is one of major side-effect of many conventional chemotherapy. For example, at low dose, cyclophosphamide can be used to treat immune diseases such as multiple sclerosis, rheumatoid arthritis and the suppression of transplant rejections. (Emadi A, et al, Nat Rev Clin Oncol. 2009 November; 6(11):638-47; Perini P, et al. Neurol Sci. 2008 September; 29 Suppl 2:S233-4.) and is also widely used in bone marrow transplantation "conditioning" and "mobilization" regimens, and for the treatment of refractory severe autoimmune conditions, such as systemic lupus erythematosus (SLE), minimal change disease, severe rheumatoid arthritis, Wegener's granulomatosis (with trade name Cytoxan), scleroderma, and multiple sclerosis (with trade name Revimmune). In addition, HDAC has recently emerging as a promising target for treating immune disease [Szyf M. Clin Rev Allergy Immunol. 2010 August; 39(1):62-77]. Therefore it is not difficult to imagine the compositions of present invention could be used for treatment of an immune disease.

In a preferred embodiment, the immune disease is selected from the group consisting of the rejection of transplanted organs and tissues, a graft-versus-host disease, a non-autoimmune inflammatory disease, and an autoimmune disease, wherein said autoimmune disease is selected from the group consisting of acute disseminated encephalomyelitis, addison's disease, ankylosing spondylitis, antiphospholipid antibody syndrome, autoimmune hemolytic anemia, autoimmune hepatitis, autoimmune inner ear disease, bullous pemphigoid, coeliac disease, chagas disease, chronic obstructive pulmonary disease, churg-strauss syndrome, dermatomyositis, Crohn's disease, diabetes mellitus type 1, endometriosis, goodpasture's syndrome, graves' disease, guillain-barrë syndrome, hashimoto's disease, hidradenitis suppurativa, idiopathic thrombocytopenic purpura, interstitial cystitis, lupus erythematosus, morphea, multiple sclerosis, myasthenia gravis, narcolepsy, neuromyotonia, pemphigus vulgaris, pernicious anaemia, polymyositis, primary biliary cirrhosis, psoriasis, psoriatic arthritis, rheumatoid arthritis, schizophrenia, scleroderma, temporal arteritis, vasculitis, vitiligo, and wegener's granulomatosis.

It should be understood that the invention is not limited to the particular embodiments shown and described herein, but that various changes and modifications may be made without departing from the spirit and scope of the invention as defined by the claims.

Synthetic Methods

The compounds of the inventions may be prepared by any process known in the field. Necessary starting materials may be obtained by standard procedures of organic chemistry. The compounds and processes of the present invention will be better understood in connection with the following representative synthetic schemes, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

In general, compounds of

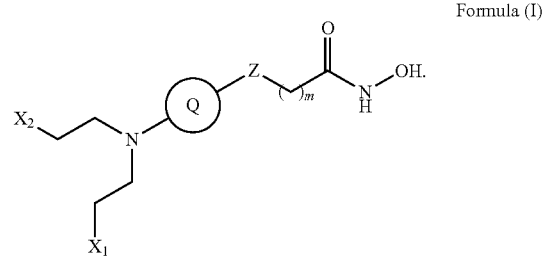

Formula (I)

can be prepared according to general Scheme 1 below. $X_1$, $X_2$, Q, Z, and m in general Scheme 1 are the same as those described in the Summary section above.

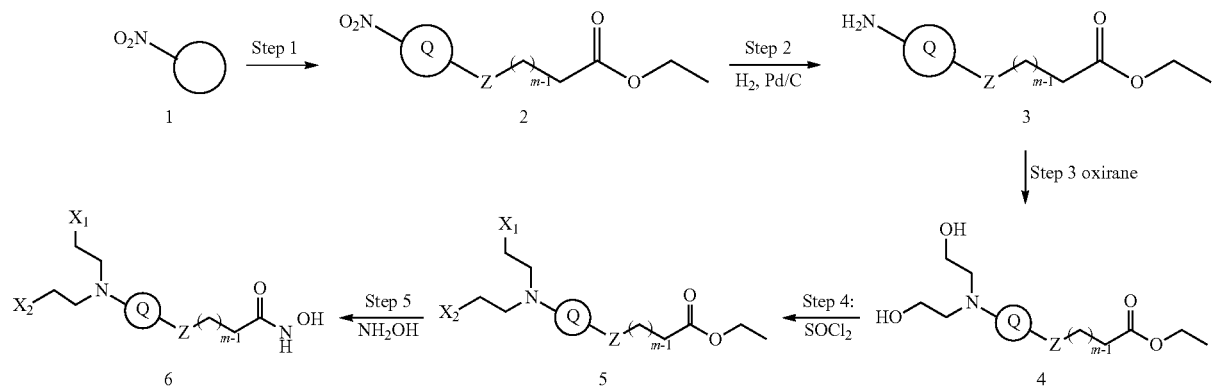

The starting material (1), a nitro-substituted 5-10 membered ring, can couple with an appropriate carboxylic ester to give intermediate (2), which can be subsequently reduced, for example with $H_2$, Pd/C, to an amino-substituted intermediate (3). The resulting intermediate (3) can react with oxirane to easily afford intermediate (4), which can be converted to intermediate (5) with high yield by reaction with a chlorinating reagent such as thionyl chloride or phosphorus pentachloride. Finally the hydroxylamination of intermediate (5) in $NH_2OH$ can afford the target compound (6).

Compounds of

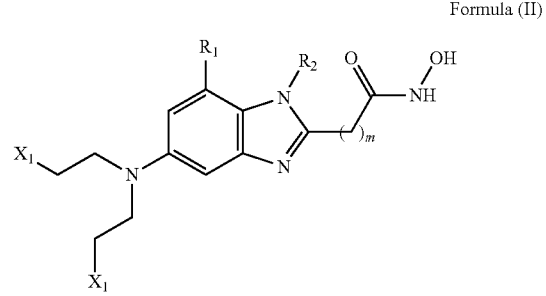

Formula (II)

can be prepared according to general Scheme 2 below. $X_1$, $R_1$, $R_2$, Z, and m in general Scheme 2 are the same as those described in the Summary section above.

Scheme 2

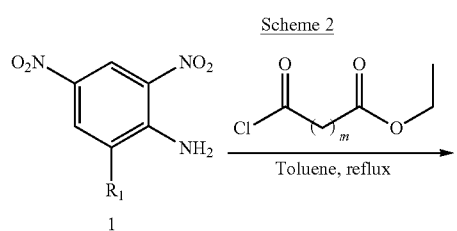
1

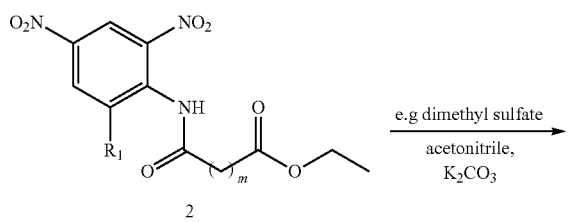
2

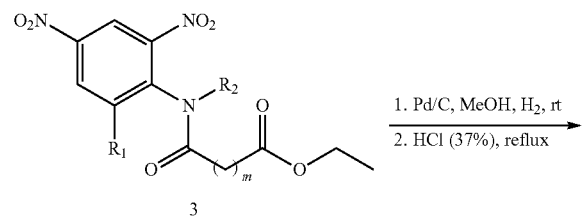
3

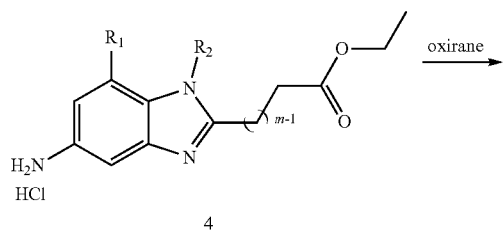
4

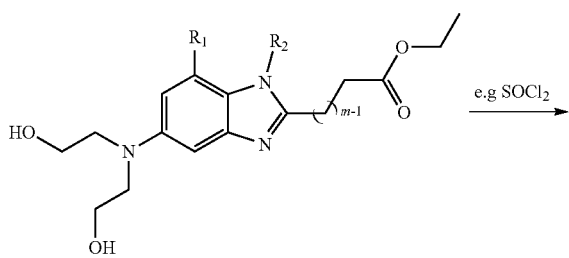
5

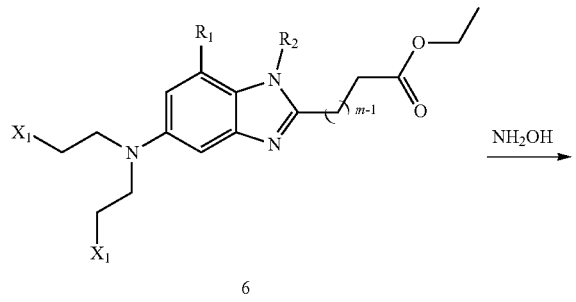
6

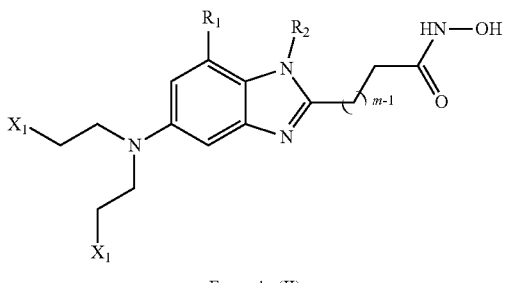

Formula (II)

The starting material (1), a substituted 2,4-dinitroaniline can couple with an appropriate acyl chloride to give a N-acylated intermediate (2). The alkylation of N-acylated intermediate (2) with an alkylation agent such as iodomethane, methyltosylate, dimethylsulfate will lead to a dinitroaromatic intermediate (3). The reduction of intermediate (3), for example with $H_2$, Pd/C, followed by dehydration with acid will form benzimidazole intermediate (4). The intermediate (4) can react with oxirane to easily afford intermediate (5), which can be converted to intermediate (6) with high yield by reaction with a chlorinating reagent such as thionyl chloride or phosphorus pentachloride. Finally the hydroxylamination of intermediate (6) in $NH_2OH$ can afford the target compound represented by formula (II).

Compound of

Formula (III)

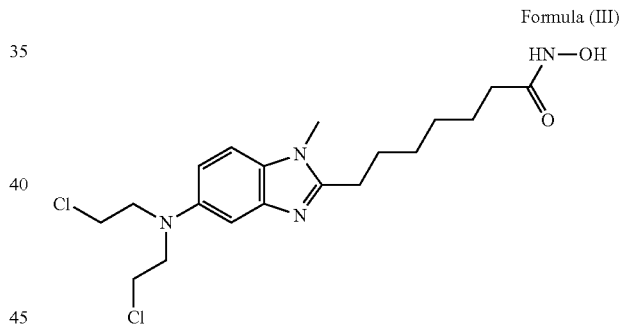

can be prepared according to general Scheme 3 below.

Scheme 3

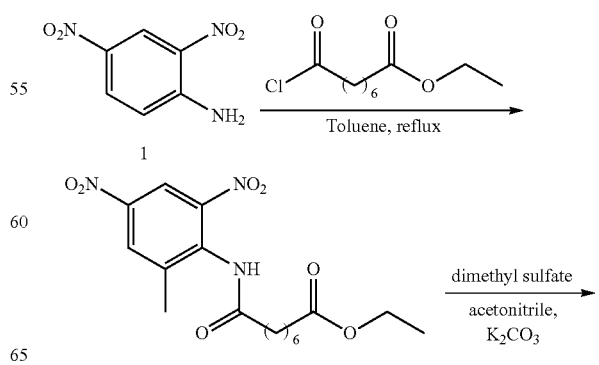
1

2

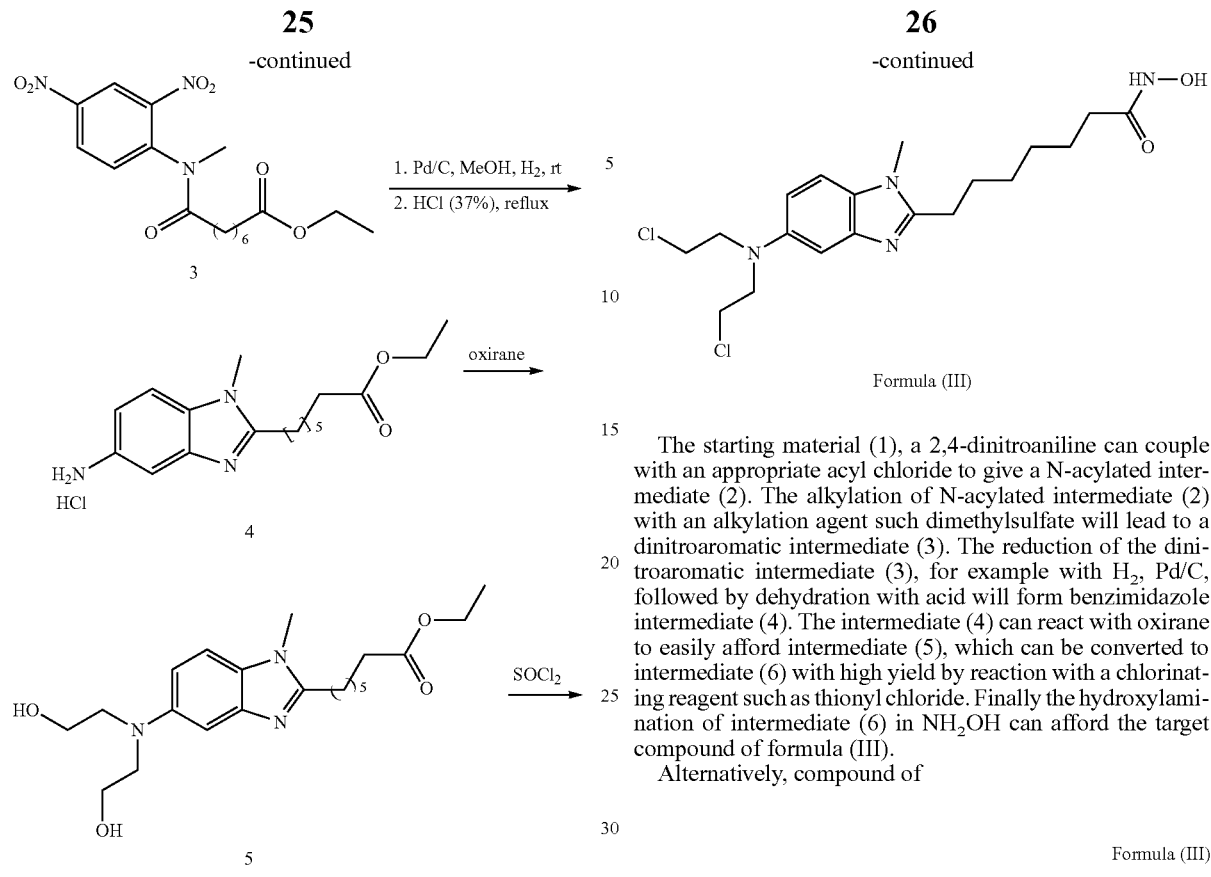

The starting material (1), a 2,4-dinitroaniline can couple with an appropriate acyl chloride to give a N-acylated intermediate (2). The alkylation of N-acylated intermediate (2) with an alkylation agent such dimethylsulfate will lead to a dinitroaromatic intermediate (3). The reduction of the dinitroaromatic intermediate (3), for example with H₂, Pd/C, followed by dehydration with acid will form benzimidazole intermediate (4). The intermediate (4) can react with oxirane to easily afford intermediate (5), which can be converted to intermediate (6) with high yield by reaction with a chlorinating reagent such as thionyl chloride. Finally the hydroxylamination of intermediate (6) in NH₂OH can afford the target compound of formula (III).

Alternatively, compound of can be prepared according to general Scheme 4 below.

27
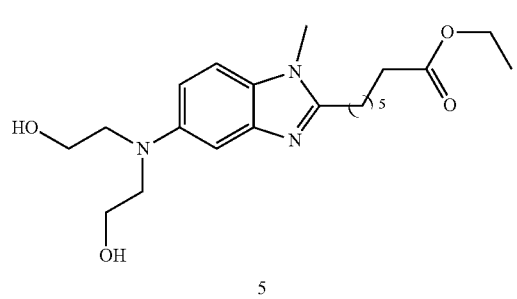
28
-continued
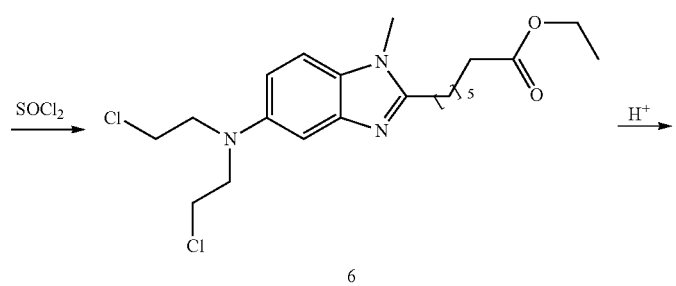
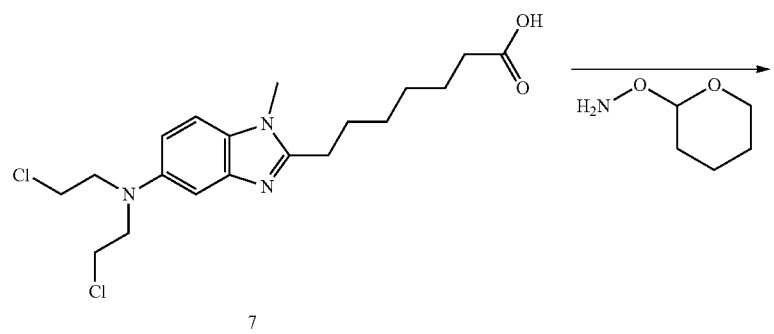
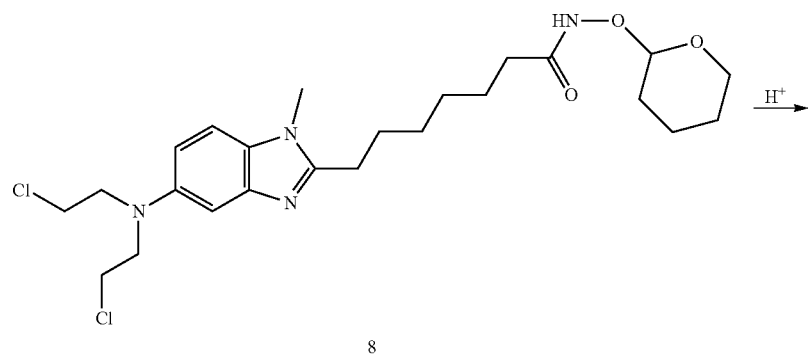
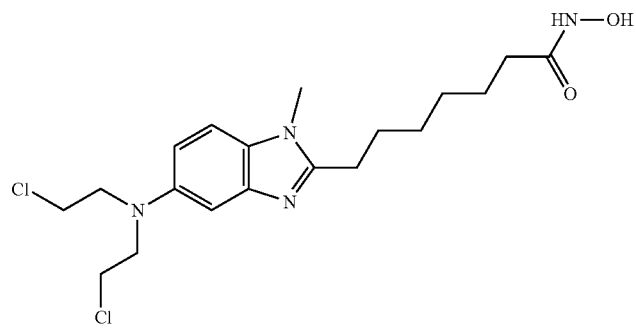
Formula (III)

The starting material (1), a 2,4-dinitroaniline can couple with an appropriate acyl chloride to give a N-acylated intermediate (2). The alkylation of N-acylated intermediate (2) with an alkylation agent such dimethylsulfate will lead to a dinitroaromatic intermediate (3). The reduction of the dinitroaromatic intermediate (3), for example with H₂, Pd/C, followed by dehydration with acid will form benzimidazole intermediate (4). The intermediate (4) can react with oxirane to easily afford intermediate (5), which can be converted to intermediate (6) with high yield by reaction with a chlorinating reagent such as thionyl chloride. The hydrolysis of intermediate (6) in concentration HCl will lead to the carboxylic acid intermediate (7); which can couple with O-(tetrahydro-2H-pyran-2-yl)hydroxylamine to afford intermediate (8). Finally, the hydrolysis of intermediate (8) in acid will result the target compound of formula (III).

Alternatively, compound of

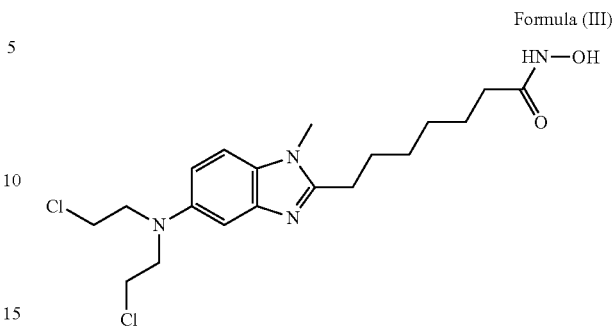

Formula (III)

can be prepared according to general Scheme 5 below.

Scheme 5

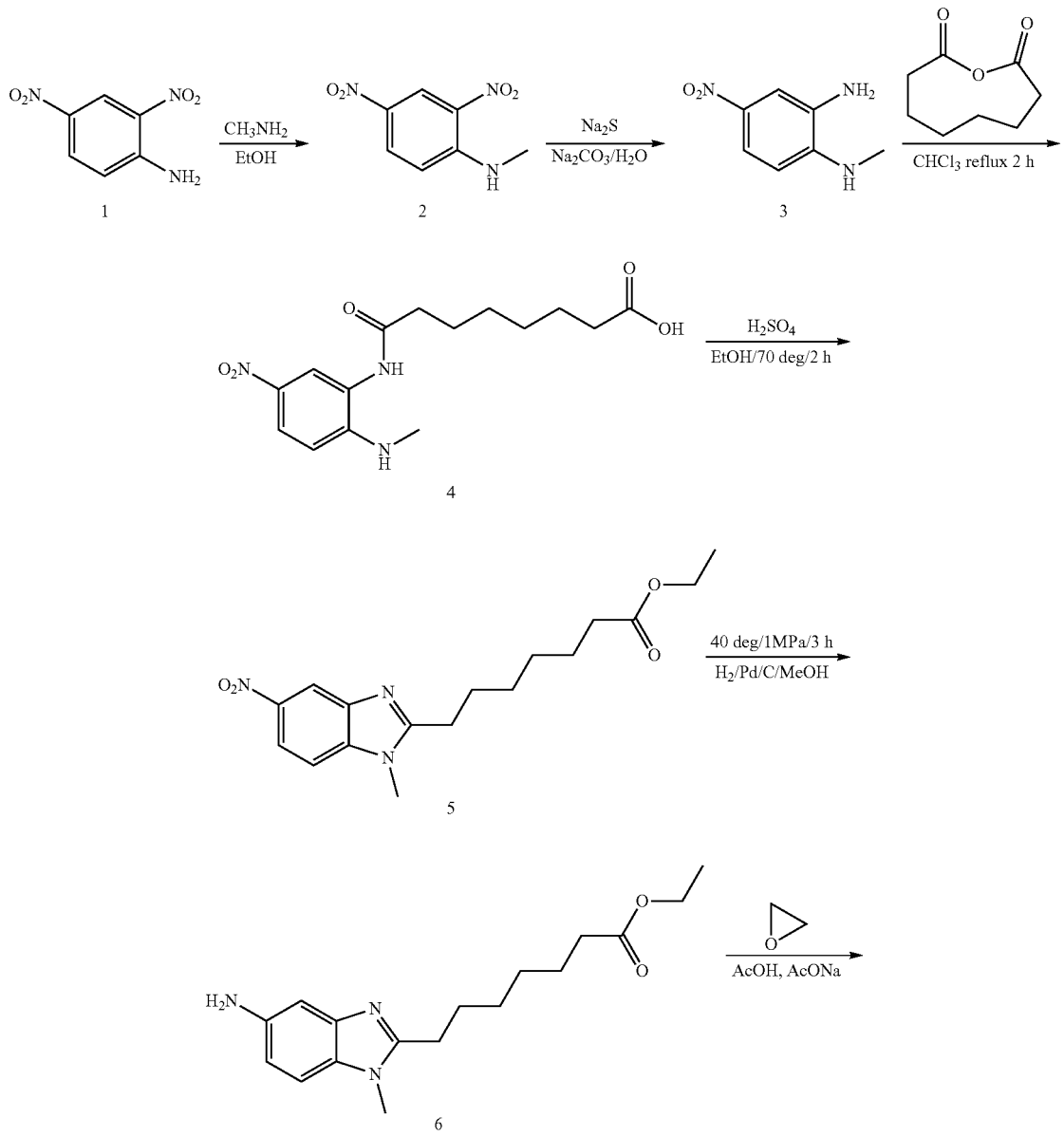

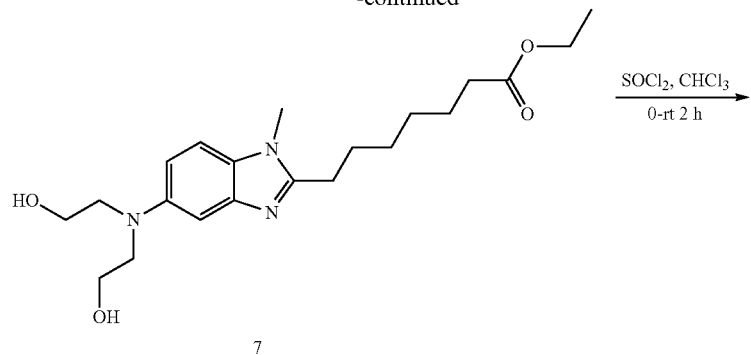

7

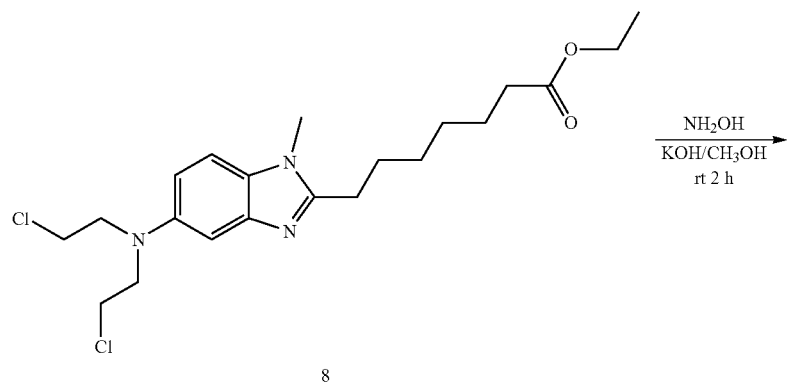

8

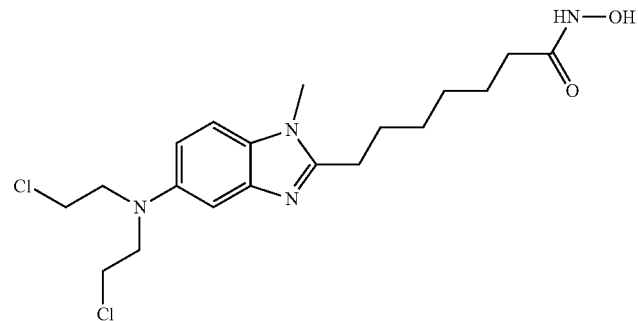

Formula (III)

The starting material (1), 1-chloro-2,4-dinitrobenzene can couple with an alkylamine to give the intermediate (2), which can be reduced to intermediate (3) with yield. The intermediate (3) can be acylated to form intermediate (4), which will undergo a dehydration reaction with acid to afford benzimidazole intermediate (5). The intermediate (5) can be subsequently reduced, for example with $H_2$, Pd/C, to an amino-substituted intermediate (6). The resulting intermediate (6) can react with oxirane to easily afford intermediate (7), which can be converted to intermediate (8) with high yield by reaction with a chlorinating reagent such as thionyl chloride or phosphorus pentachloride. Finally the hydroxylamination of intermediate (8) in $NH_2OH$ can afford the target compound of Formular (III).

Alternatively, compound of

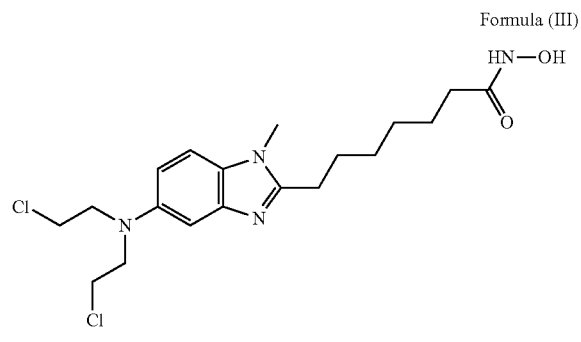 [SMILES: Cn1c(CCCCCCC(=O)NO)nc2cc(N(CCCl)CCCl)ccc21]

Formula (III)

can be prepared according to general Scheme 6 below.

Scheme 6
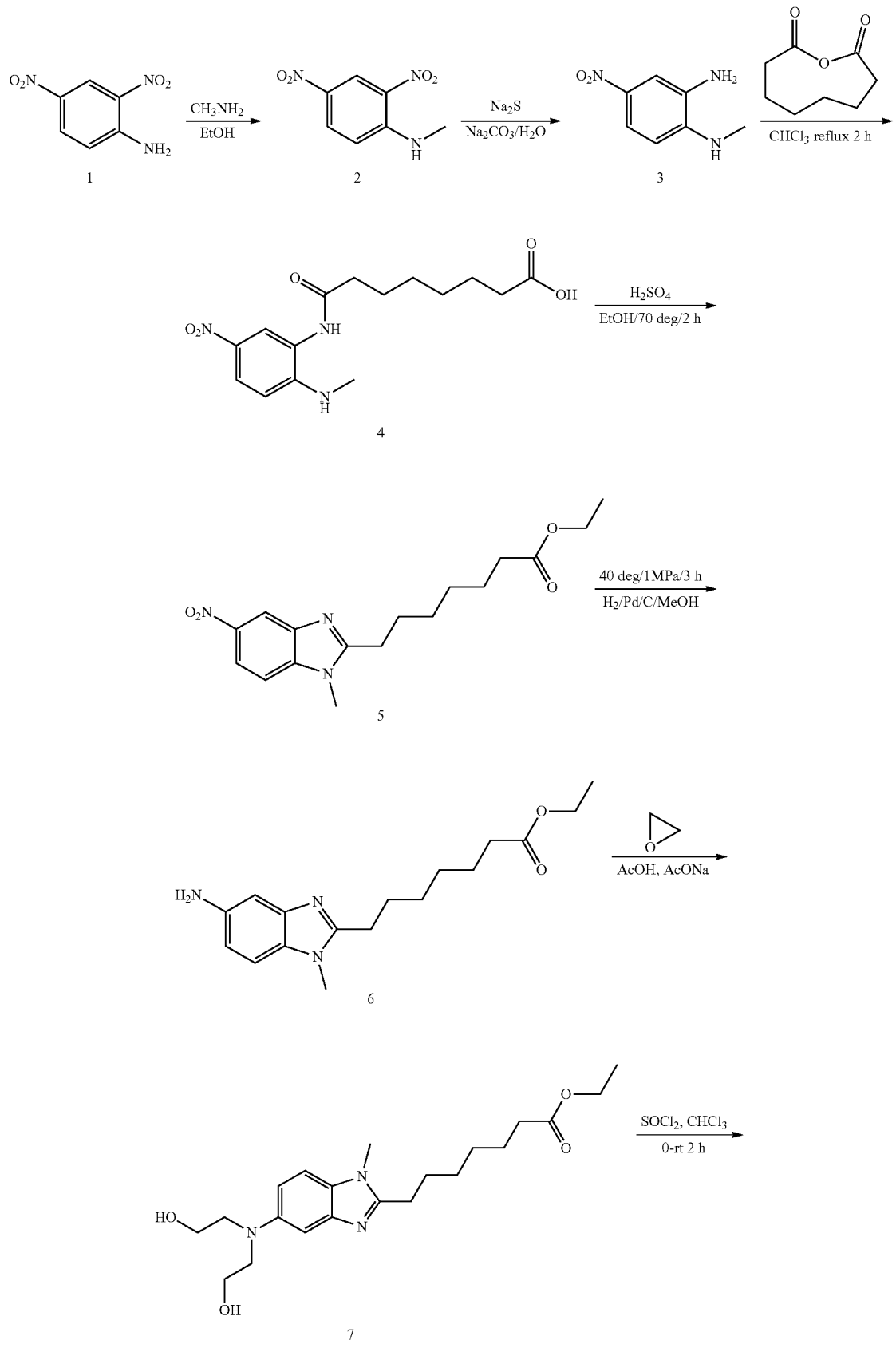

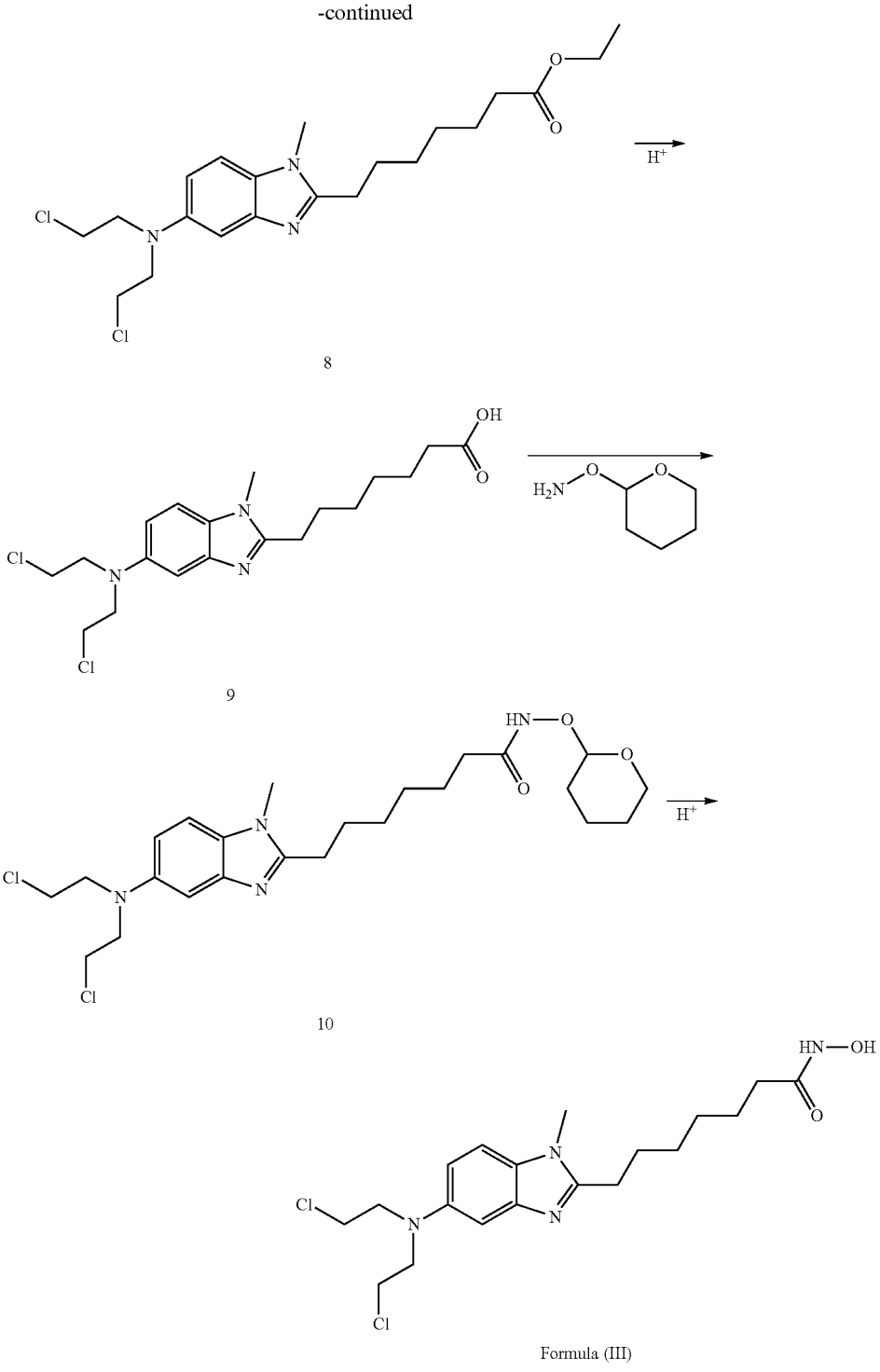

Formula (III)

The starting material (1), 1-chloro-2,4-dinitrobenzene can couple with an alkylamine to give the intermediate (2), which can be reduced to intermediate (3) with yield. The intermediate (3) can be acylated to form intermediate (4), which will undergo a dehydration reaction with acid to afford benzimidazole intermediate (5). The intermediate (5) can be subsequently reduced, for example with $H_2$, Pd/C, to an amino-substituted intermediate (6). The resulting intermediate (6) can react with oxirane to easily afford intermediate (7), which can be converted to intermediate (8) with high yield by reaction with a chlorinating reagent such as thionyl chloride or phosphorus pentachloride. The hydrolysis of intermediate (8) in concentration HCl will lead to the carboxylic acid intermediate (9), which can couple with O-(tetrahydro-2H-pyran-2-yl)hydroxylamine to afford intermediate (10). Finally, the hydrolysis of intermediate (10) in acid will result the target compound of formula (III).

EXAMPLES

Example 1

Preparation of the Formulation of Compound of Formula (III) (Also Called NL-101 First Generation Formulation)

(1) Solution 1: prepare 50% (v/v) acetic acid solution in DI water, store in room temperature;
(2) Solution 2: prepare 0.20% (w/v) NaOH solution in DI water, store in room temperature;
(3) Solution 3: prepare 200 mg/ml of compound of Formula (III) in Solution 1 (i.e. 50% acetic acid): sonication 10-30 seconds will be very helpful to dissolve the compound;
(4) Finally, add 970 uL of Solution 2 into a 30 uL Solution 3, leading to a 6 mg/ml solution of compound of Formula (III).

Example 2

Preparation a Composition of Compound of Formula (III) with Hydroxypropyl β-Cyclodextrin (Also Called HPβCD-Based NL-101 Formulation)

(1) Solution 1: prepare 50% (v/v) acetic acid solution in DI water, store in room temperature;
(2) Solution 2: prepare 20% (w/v) hydroxypropyl β-cyclodextrin by adding each 80 mL DI water into each 20 gram of hydroxypropyl β-cyclodextrin, vortex for 5 minutes, store in room temperature;
(3) Solution 3: prepare 5% (w/v) $NaHCO_3$ solution in DI water, store in room temperature; $NaHCO_3$ is used as a pH adjusting agent;
(4) Solution 4: prepare 200 mg/ml of compound of Formula(III) in Solution 1 (i.e. 50% Acetic acid): sonication 10-30 seconds will be very helpful to dissolve the compound;
(5) Solution 5: 1:1 mix of Solution 2 and Solution 3;
(6) Add 30 ul of Solution 4 into 970 uL of Solution 5 and mix well, leading to a 6 mg/ml solution of compound of Formula (III), with 10% hydroxypropyl β-cyclodextrin, 1.5% acetic acid, 2.5% $NaHCO_3$, and pH of 6-7;
(7) Filtration of the Solution: the formulations of compound of formula (III) from step (6) was filtered through a 0.2 um pre-sterilized filter with >98% recovery;
(8) Preparation of a lyophilisate: the formulations from Step (7) were lyophilized to form lyophilisate as a powder. The resulted lyophilisate formulation was chemically stable at following temperatures, −20° C., 4° C. and room temperature for at least 2 weeks. It can be stored at 4° C. for greater than 2 weeks without decomposition;
(9) Dilution study: the formulations from Step (7) were diluted with DI water (×10 fold) and were chemically stable and remained in solution without precipitation (>12 hours).

Example 3

Preparation a Composition of Compound of Formula (III) with Sulfobutylether β-Cyclodextrin (Also Called Captisol™-Based NL-101 Formulation)

(1) Solution 1: prepare 50% (v/v) acetic acid solution in DI water, store in room temperature;
(2) Solution 2: prepare 20% (w/v) sulfobutylether β-cyclodextrin by adding each 80 mL DI water into each 20 gram of sulfobutylether β-cyclodextrin, vortex for 5 minutes, store in room temperature;
(3) Solution 3: prepare 5% (w/v) $NaHCO_3$ solution in DI water, store in room temperature; $NaHCO_3$ is used here as a pH adjusting agent;
(4) Solution 4: prepare 200 mg/ml of compound of Formula(III) in Solution 1 (i.e. 50% Acetic acid): sonication 10-30 seconds will be very helpful to dissolve the compound;
(5) Solution 5: 1:1 mix of Solution 2 and Solution 3;
(6) Add 30 ul of Solution 4 into 970 uL of Solution 5 and mix well, leading to a 6 mg/ml solution of compound of Formula (III), with 10% sulfobutylether cyclodextrin, 1.5% acetic acid, 2.5% $NaHCO_3$, and pH of 6-7;
(7) Filtration of the Solution: the formulations of compound of formula (III) from step (6) was filtered through a 0.2 um pre-sterilized filter with >98% recovery;
(8) Preparation of a lyophilisate: the formulations from Step (7) were lyophilized to form lyophilisate as a powder. The resulted lyophilisate formulation was chemically stable at following temperatures, −20° C., 4° C. room temperature for at least 2 weeks. It can be stored at 4° C. for greater than 2 weeks without decomposition;
(9) Dilution study: the formulations from Step (7) were diluted with DI water (×10 fold) and were chemically stable and remained in solution without precipitation (>12 hours).

Example 4

Tris as an Alternative pH Adjusting Agent

Tris (CAS #: 77-86-1) is widely used as a component of pH buffer solution. Tris is used as excipient in some FDA approved drugs. It has a pKa of 8.30. Tris-Acetic acid buffer system has a pH range of 7-8, therefore, Tris may be idea pH adjusting agent for NIS 101 formulation.

We successfully developed a Tris containing HPBCD based NL-101 formulation with 6 mg/ml NL-101, 15% HPBCD, 250 mM Acetic acid, 333 mM Tris, pH=7.4+/−0.2. The formulation was prepared as following:
Solution 1: prepare 200 mg/ml NL-101 in 50% Acetic acid;
Solution 2: prepare 1M Tris, then dilute to 0.6666M: (Tris Base, F.W.121.14 g/mol).
Solution 3: prepare 30% (w/v) HPBCD in 100 mM sodium acetate buffer (pH=5.4);
Solution 4: 1:1 mix of Solution 2 and Solution 3.
Final solution: add 970 uL of solution 4 into 30 ul of solution 1, mix well, leading to a 6 mg/ml NL-101, 15% HPBCD, 250 mM Acetic acid, 333 mM Tris, pH=7.4+/−0.2.

As comparing to NaHCO3 as a pH adjusting agent, it is easier to accurately control the pH value of the Tris-containing HPBCD-based NL-101 formulation within the pH range of 7-8, since the Tris-containing formulation is essential a Tris-Acetic acid buffer system with a theoretic buffer range of 7-8. The neutral pH value of Tris containing HPBCD based NL-101 formulation is a clear advantage for future clinical development.

Example 5

Single Dose IV Toxicity Study in Mice with the NL-101 First Generation Formulation A single dose of NL-101 $1^{st}$ generation formulation (20, 40, 60, 80 or 100 mg/kg) was slowly administered (iv, injection time>30 seconds), to mice and change in body weight was measured over 14 day to assess toxicity of the various doses of NL-101. We found that up to 60 mg/kg of NL-101 did not result in a significant change in body weight.

However, we found that this first generation formulation has many disadvantages such as low pH value, potential precipitation after i.v. injection, and series side effects such as damaged mice tail after iv injection. More seriously, sometimes we observed that quick iv injection (e.g injection time<5 seconds) of NL-101 may lead to mice sudden death.

Example 6

Single Dose IV Toxicity Study in Mice with the HPβCD-Based NL 101 Formulation

A single dose of HPβCD-based NL-101 formulation (20, 40, 60, 80, 100, or 150 mg/kg) in 10% HPβCD was administered (iv) to mice and change in body weight was measured over 14 day to assess toxicity of the various doses of NL-101. We found that up to 60 mg/kg of NL-101 did not result in a significant change in body weight.

We are surprised to found that the HPβCD-based NL 101 formulation can significantly reduce the cardiotoxicity in vivo. The mice even can survive under quick injection (t<5 seconds) of as high as 150 mg/kg NL-101. More importantly, we didn't observe cardiorespiratory stress in mice at therapeutically effective dose of 60 mg/kg. In addition, this formulation also has many other advantages, such as neutral pH, clear and stable injection solution, no precipitate issue after iv injection, and no damaged mice tail after iv injection. Therefore, HPβCD-based NL-101 formulation will be an ideal formulation to be used in NL-101 MTD, PK, in vivo efficacy study, and IND enabling study. We are actively developing the HPβCD-based NL-101 formulation for future human clinical trial.

Example 7

Single Dose IV Toxicity Study in Mice with the Captisol™-Based NL-101 Formulation A single dose of Captisol™-based NL-101 formulation (20, 40, 60, 80, 100, or 150 mg/kg) in 10% Captisol™ was administered (iv) to mice and change in body weight was measured over 14 day to assess toxicity of the various doses of NL-101. We found that up to 60 mg/kg of NL-101 did not result in a significant change in body weight.

We are glad to found that the Captisol™-based NL-101 formulation can also significantly reduce the cardiotoxicity in vivo. The mice even can survive under quick injection (t<5 seconds) of as high as 150 mg/kg NL-101. More importantly, we didn't observe cardiorespiratory stress in mice at therapeutically effective dose of 60 mg/kg. In addition, this formulation also has many other advantages, such as neutral pH, clear and stable injection solution, no precipitate issue after iv injection, and no damaged mice tail after iv injection. Therefore, Captisol™-based NL-101 formulation will be also an ideal formulation to be used in NL-101 MTD, PK, in vivo efficacy study, IND enabling study, as well as in future human clinical trial.

Example 8

Multiple Doses IV Toxicity Study in Mice with the HPβCD-Based NL-101 Formulation Multiple doses of HPβCD-based NL-101 formulation (60 mg/kg) in 10% HPβCD was administered (iv) to mice and change in body weight was measured to assess toxicity of the various doses of NL-101. We found that mice can well tolerate multiple doses of 60 mg/kg of NL-101 without significant change in body weight. For example, the mice can be dosed at 60 mg/kg at day 1, 4, 8, 11, 18, 25. Another feasible dosing scheme is 60 mg/kg at day 1, 2, 8, 15, 22, 29.

Example 9

Multiple Doses IV Toxicity Study in Mice with the Captisol™-Based NL-101 Formulation Multiple doses of Captisol™-based NL-101 formulation (60 mg/kg) in 10% Captisol™ was administered (iv) to mice and change in body weight was measured to assess toxicity of the various doses of NL-101. We found that mice can well tolerate multiple doses of 60 mg/kg of NL-101 without significant change in body weight. For example, the mice can be dosed at 60 mg/kg at day 1, 4, 8, 11, 18, 25. Another feasible dosing scheme is 60 mg/kg at day 1, 2, 8, 15, 22, 29.

Example 10

Efficacy of HPβCD-based NL-101 formulation on Human Non-Small Cell Lung Cancer A549 Xenograft Model Animal: The balb/c mice aged 5 to 6 weeks were kept 5 per cage with an air filter cover under light (12 light/dark cycle, light on at 6H00) and temperature ($22\pm1°$ C.)-controlled environment. All manipulations of animals were performed under a sterilized laminar hood. The animals had ad libitum access to Purina mouse chow (Pro Lab PMH 4018, Trademark of Agway, Syracuse, N.Y.) and water. These animal studies were conducted according to the "Guidelines for Care and Use of Experimental Animals".

Tumor Cell Culture: Human NSCLC A549 cells were cultured in the appropriated culture medium. The cells were harvested in their logarithmic growth phase for the preparation of tumor implantation.

Tumor Implantation: human tumor cells (2.5 to $5.0\times10^6$ cells) were implanted subcutaneously in 0.2 mL of medium containing 30% Matrigel on the two flanks of balb/c nu/nu mice through a 1 to 2 cm long 20-gauge needle.

Treatments: 2 to 3 weeks after tumor cell implantation, animals that developed s.c. solid tumors were selected and divided into several homogeneous groups (n=6 animals per group or dose) with respect to tumor size (100-200 $mm^3$). The animals were i.v. dosed with 60 mg/kg of the following formulation at day 1, 4, 8, 11, 18, 25.

1. Vehicle group: 10% HPβCD, 1.5% acetic acid, 2.5% $NaHCO_3$;
2. NL-101 group: 6 mg/ml, 10% HPβCD, 1.5% acetic acid, 2.5% $NaHCO_3$;
3. Bendamustine group: 6 mg/ml, 10% HPβCD, 1.5% acetic acid, 2.5% $NaHCO_3$;

Efficacy Evaluation: subcutaneous solid tumor measurements were performed on the day of first injection and at 4-day intervals thereafter. The two largest perpendicular diameters of each tumor were measured with calipers and tumor sizes were estimated using the formula:

TV=L×W/2 where TV: tumor volume; L: length; W: width. The body weights of animals were also noted. The results are presented in Table below.

| Group | Animal (start) | Animal (end) | Body weight (g) | Tumor weight (g) | Tumor volume (mm3) | T/C (%) |
|---|---|---|---|---|---|---|
| Control | 10 | 10 | 28.8 ± 1.7 | 1.94 ± 0.3 | 2080.8 ± 552.8 | / |
| NL-101 | 6 | 6 | 27.6 ± 2.9 | 0.88 ± 0.2* | 772.7 ± 235.6* | 37.7 |
| Bendamustine | 6 | 6 | 28.6 ± 1.9 | 1.97 ± 0.5 | 1716.5 ± 550.6 | 71.9 |

*p < 0.01 vs Control group

The above data shows that HPβCD-based NL-101 composition has excellent in vivo efficacy in A549 xenograft model without evidence of significant general cytotoxicity and cardiotoxicity.

After extensive evaluation, the HPβCD-based NL-101 formulation has been selected for ND enabling study.

What is claimed is:

1. A pharmaceutical composition comprising (a) a cyclopolysaccharide, and (b) a compound of Formula (I)

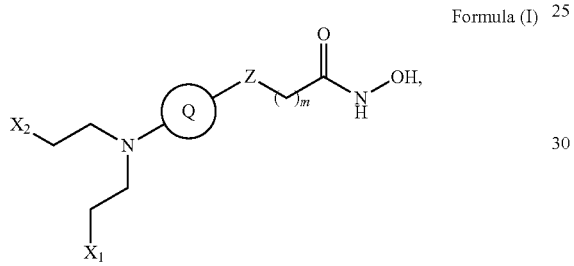

Formula (I)

or a pharmaceutically acceptable salt thereof:
wherein
m is 5, 6, 7, 8, 9, 10, 11, 12, 13, 14, 15, or 16;
Z is deleted, C($R_a R_b$), O, S, C(O), N($R_a$), SO$_2$, OC(O), C(O)O, OSO$_2$, S(O$_2$)O, C(O)S, SC(O), C(O)C(O), C(O)N($R_a$), N($R_a$)C(O), S(O$_2$)N($R_a$), N($R_a$)S(O$_2$), OC(O)N($R_a$), N($R_a$)C(O)O, N($R_a$)C(O)S, or N($R_a$)C(O)N($R_b$), in which each of $R_a$ and $R_b$, independently, is H, alkyl, alkenyl, or alkynyl;
$X_1$ and $X_2$ independently, is halo or OSO$_2R_c$, in which $R_c$ is alkyl, alkenyl, or alkynyl; and
Q is cycloalkyl, heterocycloalkyl, cycloalkenyl, heterocycloalkenyl, aryl, or heteroaryl, each of which, independently, is optionally substituted with alkyl, alkenyl, alkynyl, cycloalkyl, heterocycloalkyl, cycloalkenyl, heterocycloalkenyl, aryl, heteroaryl, halo, nitro, oxo, —C=NH, cyano, alkyl-$R_d$, O$R_d$, OC(O)$R_d$, OC(O)O$R_d$, OC(O)S$R_d$, S$R_d$, C(O)$R_d$, C(O)O$R_d$, C(O)S$R_d$, C(O)N$R_eR_f$, SO$R_d$, SO$_2R_d$, N$R_eR_f$, or N($R_e$)C(O)$R_f$, in which each of $R_d$, $R_e$, and $R_f$, independently, is H, alkyl, alkenyl, alkynyl, cycloalkyl, heterocycloalkyl, aryl, heteroaryl, halo, cyano, amine, nitro, hydroxy, or alkoxy.

2. The composition of claim 1, wherein $X_1$ and $X_2$ independently, is halo; Z is deleted, CH$_2$, O, CO, NH, SO$_2$, OC(O), C(O)O, C(O)S, NHC(O), C(O)NH, OC(O)NH, NHC(O)O, or NHC(O)S; m is 5, 6, 7, or 8; and Q is a 9-10 membered aryl or heteroaryl.

3. The composition of claim 2 wherein the compound is represented by Formula(II)

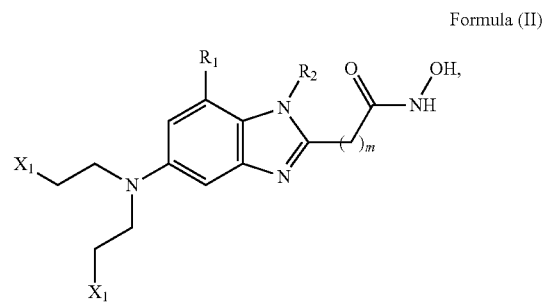

Formula (II)

in which $R_1$ and $R_2$ independently, is H, alkyl, alkenyl, alkynyl, cycloalkyl, heterocycloalkyl, halo, —C=NH, amine, cyano, hydroxy, or alkoxy.

4. The composition of claim 3, wherein the compound is represented by Formula(III)

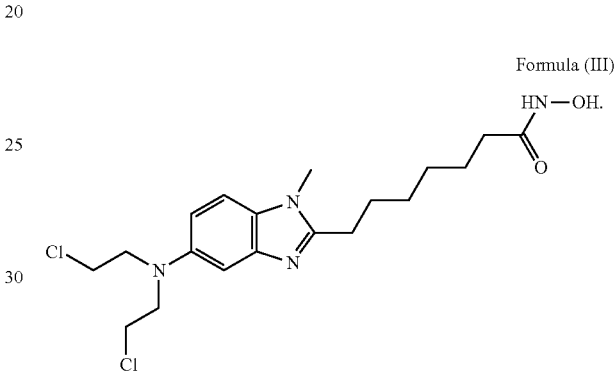

Formula (III)

5. The composition of claim 1 wherein said pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, biocarbonate, carbonate, sodium hydroxide salt, calcium hydroxide salt, potassium hydroxide salt, tromethamine(Tris) salt, or mixtures thereof.

6. The composition of claim 5 wherein said pharmaceutically acceptable salt is a hydrochloride salt, methanesulfonate, toluenesulfonate, acetate, succinate, citrate, maleate, tartrate, or mixtures thereof.

7. The composition of claim 6 wherein said pharmaceutically acceptable salt is an acetate salt.

8. The composition of claim 1 wherein the cyclopolysaccharide is a cyclodextrin.

9. The composition of claim 8 wherein said cyclodextrin is selected from the group consisting of α-cyclodextrin, βcyclodextrin, δ-cyclodextrin.

10. The composition of claim 9 wherein said cyclodextrin is β-cyclodextrin.

11. The composition of claim 10 wherein β-cyclodextrin is a hydroxypropyl β-cyclodextrin, or sulfobutylether β-cyclodextrin.

12. The composition of claim 10, wherein said β-cyclodextrin is a β-cyclodextrin substituted with 2-hydroxy-N,N,N-trimethylpropanammonium, carboxymethylated-β-cyclodextrin, O-phosphated-β-cyclodextrin, succinyl-(2-hydroxy)propyl-β-cyclodextrin, sulfopropylated-β-cyclodextrin, heptakis(6-amino-6-deoxy)-β-cyclodextrin, O-sulfated-β-cyclodextrin, and δ-monodeoxy-6-mono-(3-hydroxy)propylamino-β-cyclodextrin.

13. The composition of claim 1 wherein the composition further contains a pH adjusting agent selected from the group consisting of acids, bases and salts, or mixtures thereof, for adjusting the pH range of the composition.

14. The composition of claim 13 wherein said pH adjusting agent is sodium bicarbonate, sodium carbonate, sodium hydroxide, potassium hydroxide, calcium hydroxide, tromethamine (Tris), or mixtures thereof.

15. The composition of claim 14 wherein said pH adjusting agent is a sodium bicarbonate, tromethamine (Tris), or mixtures thereof.

16. A composition comprising (a) a cyclodextrin, (b) a compound of Formula (III)

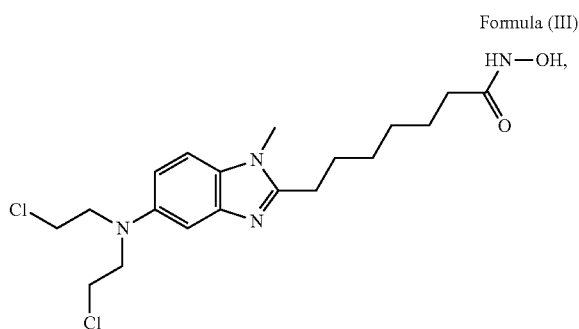 [SMILES: Cn1c(CCCCCCC(=O)NO)nc2cc(N(CCCl)CCCl)ccc21]

Formula (III)

or a pharmaceutically acceptable salt thereof, and (c) a pH adjusting agent selected from the group consisting of acids, bases and salts, or mixtures thereof, for adjusting the pH range of the composition.

17. The composition of claim 16 wherein said cyclodextrin is β-cyclodextrin.

18. The composition of claim 17, wherein said β-cyclodextrin is a β-cyclodextrin substitued with 2-hydroxy-N,N,N-trimethylpropanammonium, carboxymethylated-β-cyclodextrin, O-phosphated-β-cyclodextrin, succinyl-(2-hydroxy)propyl-β-cyclodextrin, sulfopropylated-β-cyclodextrin, heptakis(6-amino-6-deoxy)-β-cyclodextrin, O-sulfated-β-cyclodextrin, and 6-monodeoxy-6-mono-(3-hydroxy)propylamino-β-cyclodextrin.

19. The composition of claim 17 wherein said β-cyclodextrin is hydroxypropyl β-cyclodextrin, or sulfobutylether β-cyclodextrin.

20. The composition of claim 16 wherein said pharmaceutically acceptable salt is a hydrochloride salt, methanesulfonate, toluenesulfonate, acetate, succinate, citrate, maleate, tartrate, or mixtures thereof.

21. The composition of claim 16 wherein said pharmaceutically acceptable salt is an acetate salt.

22. The composition of claim 16 wherein said pH adjusting agent is bicarbonate, carbonate, sodium hydroxide, calcium hydroxide, potassium hydroxide, tromethamine, or mixtures thereof.

23. The composition of claim 16 wherein said pH adjusting agent is a sodium bicarbonate.

24. The composition of claim 17 wherein said β-cyclodextrin is a hydroxypropyl β-cyclodextrin or sulfobutylether β-cyclodextrin, said pharmaceutically acceptable salt is an acetate salt, and said pH adjusting agent is sodium bicarbonate.

25. The composition of claim 16 wherein the composition has a pH range from 6.0 to 9.0.

26. The composition of claim 25 in which the pH range of the composition is from 7.0 to 8.0.

27. The composition of claim 16 wherein the cyclodextrin is present at a concentration from 2.5% to 40% weight/volume.

28. The composition of claim 16 wherein the cyclodextrin is present at a concentration from 5% to 20% weight/volume.

29. A pharmaceutical dosage form comprising a pharmaceutical composition according to claim 16, wherein the pharmaceutical dosage form comprises 5 mg to 500 mg of compound represented by Formula (III).

30. A lyophilized preparation of the composition according to claim 16, wherein the preparation is packaged in a vial or other pharmaceutically acceptable container.

31. A method of treating a neoplastic disease or an immune disease comprising administering, either alone or in combination with other therapies, to a subject having the neoplastic disease or immune disease an effective amount of the composition according to claim 16, wherein said neoplastic disease is lung cancer, head and neck cancer, central nervous system cancer, prostate cancer, testicular cancer, colorectal cancer, pancreatic cancer, liver cancer, stomach cancer, biliary tract cancer, esophageal cancer, gastrointestinal stromal tumor, breast cancer, cervical cancer, ovarian cancer, uterine cancer, leukemia, lymphomas, multiple myeloma, melanoma, basal cell carcinoma, squamous cell carcinoma, bladder cancer, renal cancer, sarcoma, mesothelioma, thymoma, myelodysplastic syndrome, or myeloproliferative disease.

32. A method of treating according to claim 31, wherein said neoplastic disease is leukemia, lymphomas, multiple myeloma, lung cancer, breast cancer, myelodysplastic syndrome, myeloproliferative disease, pancreatic cancer, liver cancer, stomach cancer, esophageal cancer, gastrointestinal stromal tumor, cervical cancer, ovarian cancer, uterine cancer, or melanoma.

* * * * *